United States Patent [19]

Hosoi et al.

[11] Patent Number: 4,743,609
[45] Date of Patent: May 10, 1988

[54] INDOLE DERIVATIVES HAVING GASTRIC AND ANTISECRETORY AND CYTOPROTECTIVE PROPERTIES, AND PHARMACEUTICAL PREPARATIONS CONTAINING SAME

[75] Inventors: Masaaki Hosoi, Kawasaki; Fumio Nakano, Okazaki; Kenji Matsuyama, Ichikawa; Hiroshi Takeshita, Ichikawa; Kenji Niiyama, Ichikawa; Susumu Nakagawa, Okazaki, all of Japan

[73] Assignee: Banyu Pharmaceutical Co., Ltd., Tokyo, Japan

[21] Appl. No.: 827,898

[22] Filed: Feb. 10, 1986

[30] Foreign Application Priority Data

Feb. 12, 1985 [JP] Japan ............................... 60-23585
Nov. 14, 1985 [JP] Japan ............................... 60-253643

[51] Int. Cl.$^4$ ................. C07D 401/12; A61K 31/405
[52] U.S. Cl. ................................. 514/339; 514/318; 514/253; 514/228.2; 514/235.2; 546/273; 546/193; 544/360; 544/131; 544/124; 544/58.6; 544/62

[58] Field of Search ............... 546/273, 193; 544/360, 544/131, 124, 58.6, 62; 514/339, 318, 253, 228, 222

[56] References Cited

U.S. PATENT DOCUMENTS 4,575,554  3/1986  Sih ........................................ 546/271

Primary Examiner—Jane T. Fan
Attorney, Agent, or Firm—Larson and Taylor

[57] ABSTRACT

This invention provides a class of new indole derivatives which are useful as medicinal compounds having a mild inhibitory effect on the gastric acid secretion as well as a remarkably cytoprotective effects on gastric muscosa, and which are represented by the general formula:

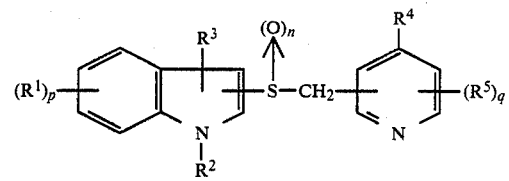

29 Claims, No Drawings

INDOLE DERIVATIVES HAVING GASTRIC AND ANTISECRETORY AND CYTOPROTECTIVE PROPERTIES, AND PHARMACEUTICAL PREPARATIONS CONTAINING SAME

SUMMARY OF THE INVENTION

This invention relates to a new indole derivative which is useful as an agent of treating therapeutically gastric ulcer or duodenal ulcer in mammalian animals. This invention also relates to a process for the production of the new indole derivative. This invention further relates to a pharmaceutical composition for therapeutic treatment of gastrointestinal ulcer.

BACKGROUND OF THE INVENTION

In one of the known methods of treating therapeutically gastrointestinal inflammatory diseases, especially the gastric ulcer or the duodenal ulcer, the administration of a medicinal compound having an activitiy to inhibit the secretion of gastric acid is performed. The medicinal compound administered for that purpose includes cimetidine (see "Merck Index" 10th Edition, Monograph No. 2254) which is known as an antagonist to the histamine $H_2$-receptors. Recently, it was discovered that the secretion of gstric acid is governed by an enzyme, $H^+$, $K^+$-ATPase having the specific property that this enzyme can be activated by potassium cation. It is thus revealed that an inhibitor to said enzyme may be useful as an agent of inhibiting or suppressing the secretion of gastric acid and hence be useful as an agent of treating therapeutically the ulcer in the gastrointestinal tract (see a Japanese medicinal journal "I-gaku no Ayumi" Vol. 128, page 296 (1984); a Japanese medicinal journal "Sa-i-shin I-gaku" Vol. 37, page 481 (1982); the "Nature" Vol. 290, 159–161 (March 1981) and "Drugs" Vol. 25, 315–330 (1983). As example of the known compounds having the activity to inhibit the $H^+$, $K^+$-ATPase is mentioned a group of benzimidazole derivatives which is typically represented by omeprazole (identified as 2-[(3,5-dimethyl-4-methoxy-2-pyridyl)methylsulfinyl]-5-methoxybenzimidazole (see Japanese patent application first publication "Kokai" No. 141783/79; U.S. Pat. No. 4,255,431; No. 4,337,257 and No. 4,508,905). It is also known that some of the above-mentioned benzimidazole derivatives exhibit an activity to effect the gastrointestinal cytoprotection (see Japanese patent application first publication "Kokai" No. 53406/82; U.S. Pat. No. 4,359,465).

The antagonists to the histamine $H_2$-receptors which are typically represented by cimethidine, as well as the inhibitors to the $H^+$, $K^+$-ATPase which are typically represented by omeprazole show a high activity to inhibit the secretion of gastric acid, and owing to this activity, they are able to exhibit good curative effects in the therapeutic treatment of the gastric ulcer. However, it has often been observed that when the ulcer has been cured through the administrations of the aforesaid drug and thus the administration of the drug is stopped, the ulcer is very much likely to return with the lapse of time after the stoppage of the drug administration. Therefore, it is not worthy to say that cimetidine and omeprazole are a fully satisfactory drug for therapeutic treatment of the gastrointestinal ulcers.

Accordingly, it has been a lasting demand to exploit a better antiulcer drug effective in the therapeutic treatment of gastrointestinal ulcers. We, the present inventors, have paid our attention on indole derivatives, and we have made extensive researches in an attempt to provide a class of new indole derivatives which exhibit the activity to inhibit the gastric acid secretion and are useful as an antiulcer agent having such further advantages that long successive administrations of the drug to the patients is allowable and the relapse or return of the ulcer as once healed is effectively prevented even after the stopped administration of the durg. As a result, we have succeeded in synthetizing a class of new indole derivatives which have now been found by us to exhibit a mild activity of inhibiting the gastric acid secretion as well as remarkable cytoprotective effects on the gastrointestinal tract, in combination, as will be demonstrated by the pharmacological experiments shown hereinafter. Thus, we have accomplished this invention.

DETAILED DESCRIPTION OF THE INVENTION

According to a first aspect of this invention, therefore, there is provided as the new indole derivative a compound of the general formula (I):

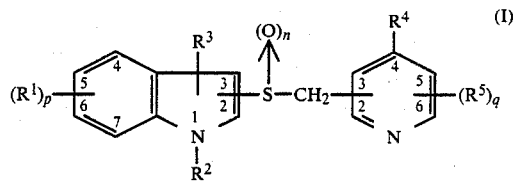

wherein $R^1$ is a hydrogen atom, a halogen atom, a lower alkyl group, a trifluoromethyl group, a lower alkoxy group, an acyl group or a lower alkoxycarbonyl group; $R^2$ is a hydrogen atom or a lower alkyl group; $R^3$ is a hydrogen atom, a lower alkyl group, a lower alkoxy group or a lower alkylthio group; $R^4$ is hydrogen atom, a lower alkyl group, a lower alkoxy group, a halogen atom, a hydroxy group, a lower alkoxycarbonyl group, a substituted or ansubstituted aralkyloxy group, or a group of the formula —$NR^aR^b$ where $R^a$ and $R^b$ are the same or different and each are a hydrogen atom or a lower alkyl group, or $R^a$ and $R^b$ taken together with the adjacent nitrogen atom form a 5-membered or 6-membered heterocyclic group containing optionally a further hetero-atom therein; $R^5$ is a hydrogen atom, a lower alkyl group, a lowr alkoxy group, an aralkyl group or a substituted or unsubstituted aralkyloxy group; and n is an integer of zero or 1, p is an integer of 1, 2, 3 or 4; and q is an integer of 1, 2 or 3, or a pharmaceutically acceptable salt of said compound.

According to a particular embodiment of the first aspect of this invention, there is provided a new compound of the formula (I'):

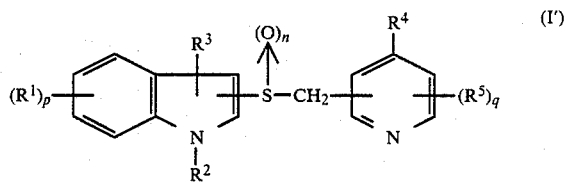

wherein $R^1$ is a hydrogen atom, a halogen atom, a lower alkyl group, a trifluoromethyl group, a lower alkoxy group, a lower alkanoyl group or a lower alkoxycarbonyl group; $R^2$ is a hydrogen atom or a lower alkyl group; $R^3$ is a hydrogen atom, a lower alkyl group or a lower alkylthio group; $R^4$ is a hydrogen atom, a lower alkyl group, a lower alkoxy group, a halogen atom, a hydroxy group, a lower alkoxycarbonyl group, an amino group, a mono-lower-alkylamino group, a di-lower-alkylamino group, or $R^4$ is a group of the formula

where $R^a$ and $R^b$ taken together form an alkylene group of 2 to 5 carbon atoms which is optionally interrupted by an oxygen atom, a sulfur atom or a nitrogen atom as the hetero-atom interposed in the chain of the alkylene group, so that $R^a$ and $R^b$ taken together with the adjacent nitrogen atom form a 5-membered or 6-membered heterocyclic group optionally containing further an oxygen atom, a sulfur atom or a nitrogen atom as the hetero-atom therein; $R^5$ is a hydrogen atom, a lower alkyl group or a lower alkoxy group; and n is zero or 1; p is 1, 2, 3 or 4; and q is 1, 2 or 3, or a pharmaceutically acceptable salt of said compound. In the compound of the above formula (I'), it is preferable that $R^4$ is particularly such a group of the formula

which forms a pyrrolidino group, a piperidino group, a morpholino group, a thiomorpholino group or a piperadino group and of which the heterocyclic group is unsubstituted or substituted by a lower alkyl group, or that $R^4$ is a group of the formula

where $R^a$ and $R^b$ each are a lower alkyl group.

The indole compound of the formula (I) according to this invention may be divided into the undermentioned four types (Ia), (Ib), (Ic) and (Id), depending on the different steps which are involved in the process for the production of them:

(i) A compound represented by the formula

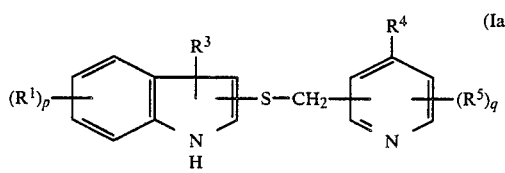

(ii) A compound represented by the formula

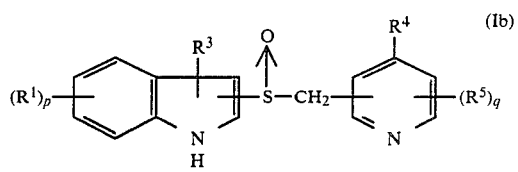

(iii) A compound represented by the formula

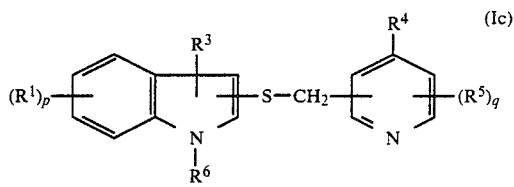

(iv) A compound represented by the formula

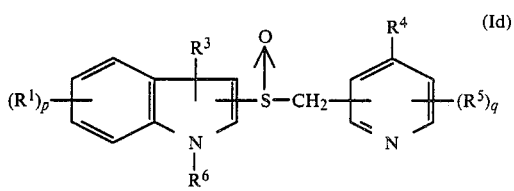

wherein $R^1$, $R^3$, $R^4$, $R^5$, p and q are as defined above and $R^6$ is a lower alkyl group.

In this specification, the various terms described here have the following meanings:

By the term "lower alkyl group" is meant a linear or branched alkyl group containing 1 to 6 carbon atoms, particularly 1–4 carbon atoms, for example, methyl, ethyl, n-propyl, isopropyl, n-butyl, iso-butyl, sec-butyl, tert-butyl, n-pentyl, isopentyl and n-hexyl groups. By the term "lower alkoxy group" is meant a linear or branched alkoxy group containing 1 to 6 carbon atoms, particularly 1–4 carbon atoms, for example, methoxy, ethoxy, n-propoxy, isopropoxy, n-butoxy, isobutoxy, sec-butoxy, tert-butoxy and n-pentoxy groups.

An "aralkyl" group includes an aralkyl group containing 7 to 12 carbon atoms, for example, a phenyl-($C_1$–$C_4$)alkyl group such as benzyl, phenetyl and phenylpropyl groups, as well as a naphthyl-($C_1$14 $C_4$)-alkyl group such as (1-naphthyl)methyl group.

The term "an acyl group" includes an alkanoyl group of 2 to 6 carbon atoms, particularly 1–4 carbon atoms, such as acetyl, propionyl and butyryl group, as well as an aroyl group such as benzoyl and toluoyl groups. The group of the formula $-NR^aR^b$ where $R^a$ and $R^b$ are as defined hereinbefore includes an amino group ($-NH_2$) and a mono-lower-alkylamino group or a di-lower-alkylamino group, for example, methylamino, dimethylamino, ethylamino, diethylamino, n-propylamino, di-n-propylamino, isopropylamino, di-isopropylamino, n-butylamino, di-n-butylamino, tert-butylamino and di-tert-butylamino groups. The group of the formula $-NR^aR^b$ further includes a 5-membered or 6-membered nitrogen-containing cyclic group optionally containing a further hetero-atom therein. In particular, the group of the formula $-NR^aR^b$ may be a cyclic group of the formula

where $R^a$ and $R^b$ taken together form an alkylene group of 2 to 5 carbon atoms containing no further hetero-atom or containing an oxygen atom or a sulfur atom or a nitrogen atom as the further hetero-atom interposed in the chain of the alkylene group, so that $R^a$ and $R^b$ taken together with the adjacent nitrogen atom form a 5-membered or 6-membered cyclic group or ring containing said adjacent nitrogen atom optionally together with or without an oxygen atom or a sulfur atom or a nitrogen atom as the further hetero-atom interposed in said ring.

When the group of the formula —$NR^aR^b$ forms a 5-membered or 6-membered nitrogen-containing heterocyclic group or a cyclic amino group, the cyclic groups may be substituted by one or more of substituents which may be a lower alkyl group or a hydroxyl group. Particular examples of such group of the formula

where $R^a$ and $R^b$ together with the adjacent nitrogen atom form the heterocyclic group or the cyclic amino group include a pyrrolidino group, a piperidino group, a morpholino group, a thiomorpholino group, a piperazino group and N-methylpiperazino group.

By the term "lower alkoxycarbonyl group" is meant an alkoxycarbonyl group containing 2 to 6 carbon atoms, for example, methoxycarbonyl, ethoxycarbonyl, n-propoxycarbonyl, isopropoxycarbonyl, n-butoxycarbonyl, iso-butoxycarbonyl, sec-butoxycarbonyl, tert-butoxycarbonyl and n-pentoxycarbonyl groups.

By the term "lower alkylthio group" is meant an alkylthio group containing 1 to 6 carbon atoms, particularly 1-4 carbon atoms, for example, methylthio, ethylthio, n-propylthio, isopropylthio, n-butylthio, isobutylthio, sec-butylthio and tert-butylthio groups.

By the term "aralkyloxy" group is meant a phenyl-($C_1$-$C_4$)alkyloxy group such as benzyloxy, phenethyloxy and phenylpropoxy groups.

The "halogen atom" includes a chlorine atom, a bromine atom, an iodine atom and a fluorine atom.

The new compound of this invention may be converted into its pharmaceutically acceptable salt, such as a pharmaceutically acceptable acid addition salt thereof by reacting with a pharmaceutically acceptable acid, for example, an inorganic acid, especially hydrochloric acid, hydrobromic acid, sulfuric acid, phosphoric acid, nitric acid and the like; and an organic acid, especially formic acid, acetic acid, propionic acid, succinic acid, glycollic acid, lactic acid, malic acid, tartaric acid, citric acid, maleic acid, phenylacetic acid, benzoic acid, salicylic acid, methanesulfonic acid, p-toluenesulfonic acid, benzenesulfonic acid and the like, including an amino acid such as aspartic acid, glutamic acid and the like.

According to preferred embodiments of the first aspect of this invention, there are provided first to seventh, preferred groups of the new compounds of the formula (I) of this invention which are as follows:

Thus, the first preferred group of the compounds (I) of this invention includes a compound of the formula (I-1):

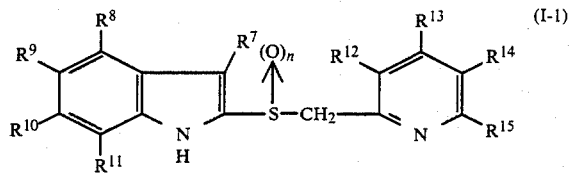

wherein $R^7$ is a hydrogen atom, an alkyl group of 1-6 carbon atoms or an alkylthio group of 1-6 carbon atoms; $R^8$, $R^9$, $R^{10}$ and $R^{11}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{12}$, $R^{13}$, $R^{14}$ and $R^{15}$ are the same or different and each are a hydrogen atom, an alkyl group of 1-6 carbon atoms or an alkoxy group of 1-6 carbon atoms; and n is zero or 1, or a pharmaceutically acceptable salt of said compound. In the compound of the formula (I-1), it is preferred that $R^7$ is a hydrogen atom, a methyl group or a methylthio group; $R^8$ and $R^{10}$ each are a hydrogen atom; $R^9$ is a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{11}$ is a hydrogen atom or a trifluoromethyl group; $R^{12}$ and $R^{14}$ each are a hydrogen atom or an alkyl group of 1-6 carbon atoms; and $R^{13}$ is an alkoxy group of 1-6 carbon atoms; $R^{15}$ is a hydrogen atom; and n is zero or 1.

The second preferred group of the compound (I) of this invention includes a compound of the formula (I-2):

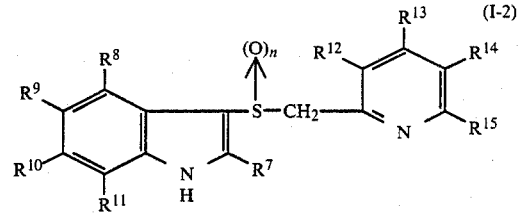

wherein $R^7$ is a hydrogen atom or an alkyl group of 1-6 carbon atoms; $R^8$, $R^9$, $R^{10}$ and $R^{11}$ are the same or different and each are a hydrogen atom, a halogen atom, an alkyl group of 1-6 carbon atoms, a trifluoromethyl group, and alkoxy group of 1-6 carbon atoms, an alkanoyl group of 2-6 carbon atoms or an alkoxycarbonyl group of 2-6 carbon atoms; $R^{12}$, $R^{13}$, $R^{14}$ and $R^{15}$ are the same or different and each are a hydrogen atom, an alkyl group of 1-6 carbon atoms or an alkoxy group of 1-6 carbon atoms; n is zero or 1, or a pharmaceutically acceptable salt of said compound.

In the compound of the formula (I-2), it is preferred that $R^7$ is a hydrogen atom or a methyl group; $R^8$ and $R^{10}$ are each a hydrogen atom; $R^9$ is a hydrogen atom, a halogen atom, an alkyl group of 1-6 carbon atoms, a trifluoromethyl group, an alkoxy group of 1-6 carbon atoms, an alkanoyl group of 2-6 carbon atoms, or an alkoxycarbonyl group of 2-6 carbon atoms; $R^{11}$ is a hydrogen atom or a trifluoromethyl group; $R^{12}$ and $R^{14}$ are each a hydrogen atom or an alkyl group of 1-6 carbon atoms; and $R^{13}$ is an alkoxy group of 1-6 carbon atoms; $R^{15}$ is a hydrogen atom; and n is zero or 1.

The third preferred group of the compound (I) of this invention includes a compound of the formula (I-3):

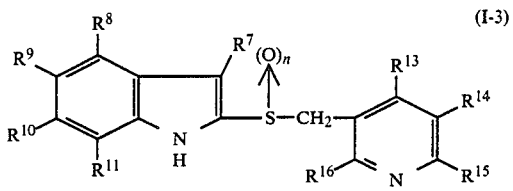

wherein $R^7$ is a hydrogen atom, an alkyl group of 1-6 carbon atoms or an alkylthio group of 1-6 carbon atoms; $R^8$, $R^9$, $R^{10}$ and $R^{11}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{13}$, $R^{14}$, $R^{15}$ and $R^{16}$ are the same or different and each are a hydrogen atom, an alkyl group of 1-6 carbon atoms or an alkoxy group of 1-6 carbon atoms; and n is zero or 1, or a pharmaceutically acceptable salt of said compound. In the compound of the formula (I-3), it is preferred that $R^7$ is a hydrogen atom, a methyl group or a methylthio group; $R^8$, $R^{10}$ and $R^{11}$ are each a hydrogen atoms; $R^9$ is a hydrogen atom, an alkyl group of 1-6 carbon atoms, a trifluoromethyl group, an alkoxy group of 1-6 carbon atoms, an alkanoyl group of 2-6 carbon atoms, or an alkoxycarbonyl group of 2-6 carbon atoms; $R^{13}$ is a hydrogen atom, an alkyl group of 1-6 carbon atoms or an alkoxy group of 1-6 carbon atoms; and $R^{14}$, $R^{15}$ and $R^{16}$ each are a hydrogen atom; and n is zero or 1.

The fourth preferred group of the compound (I) of this invention includes a compound of the formula (I-4)

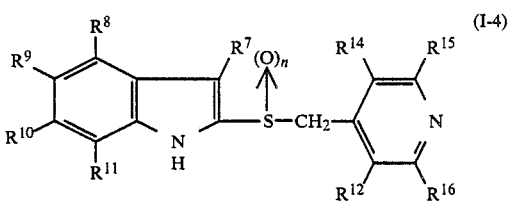

wherein $R^7$ is a hydrogen atom, a methyl group or a methylthio group; $R^8$, $R^9$, $R^{10}$ and $R^{11}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 1-6 carbon atoms; $R^{12}$, $R^{14}$, $R^{15}$ and $R^{16}$ are the same or different and each are a hydrogen atom, an alkyl group of 1-6 carbon atoms or an alkoxy group of 1-6 carbon atoms; and n is zero or 1, or a pharmaceutically acceptable salt of said compound. In the compound of the formula (I-4), it is preferred that $R^7$ is a hydrogen atom, a methyl group or a methylthio group; $R^8$, $R^{10}$ and $R^{11}$ are each a hydrogen atom; $R^9$ is a hydrogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{12}$, $R^{14}$, $R^{15}$ and $R^{16}$ are each a hydrogen atom; and n is zero or 1.

The fifth preferred group of the compound (I) of this invention includes a compound of the formula (I-5):

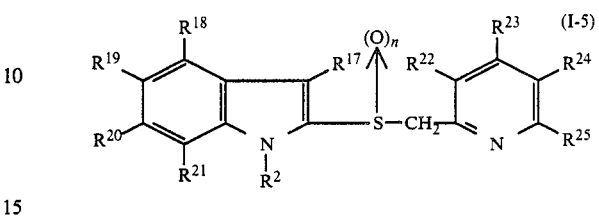

wherein $R^2$ is a hydrogen atom or an alkyl group of 1-6 carbon atoms; $R^{17}$ is a hydrogen atom or an alkyl group of 1-6 carbon atoms; $R^{18}$, $R^{19}$, $R^{20}$ and $R^{21}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{22}$, $R^{24}$ and $R^{25}$ are the same or different and each are a hydrogen atom or an alkyl group of 1-6 carbon atoms; $R^{23}$ is a group of the formula

where $R^a$ and $R^b$ are the same or different and each are a hydrogen atom or an alkyl group of 1-6 carbon atoms, or $R^a$ and $R^b$ taken together with the adjacent nitrogen atom form a 5-membered or 6-membered heterocyclic group; and n is zero or 1, or a pharmaceutically acceptable salt of said compound.

In the compound of the formula (I-5), it is preferred that $R^2$ is a hydrogen atom or a methyl or ethyl group; $R^{17}$ is a hydrogen atom or a methyl group; $R^{18}$ is a hydrogen atom or an alkyl group of 1-6 carbon atoms; $R^{19}$ is a hydrogen atom, a halogen atom, an alkyl group of 1-6 carbon atoms, a trifluoromethyl group, an alkoxy group of 1-6 carbon atoms; an alkanoyl group of 2-6 carbon atoms, or an alkoxycarbonyl group of 2-6 carbon atoms; $R^{20}$ is a hydrogen atom, an alkyl group of 1-6 carbon atoms, an alkanoyl group of 2-6 carbon atoms or a trifluoromethyl group; $R^{21}$ is a hydrogen atom, an alkyl group of 1-6 carbon atoms or a trifluoromethyl group; $R^{22}$ and $R^{24}$ are each a hydrogen atom or an alkyl group of 1-6 carbon atoms; $R^{23}$ is an amino group or a mono- or di-($C_1$-$C_6$)alkylamino group or a 5-membered or 6-membered heterocyclic group containing a nitrogen atom together with or without an oxygen atom, a sulfur atom or a further nitrogen atom as the hetero-atom; $R^{25}$ is a hydrogen atom or an alkyl group of 1-6 carbon atoms; and n is zero or 1. More preferably, the group $R^{23}$ is a piperidino group, a pyrrolidino group, a morpholino group, a thiomorpholino group, a piperazino group or N-methylpiperazino group as the heterocyclic group. Also, the group $R^{23}$ may preferably be a group of the formula

where $R^a$ and $R^b$ are each an alkyl group of 1–6 carbon atoms.

The sixth preferred group of the compound (I) of this invention includes a compound of the formula (I-6):

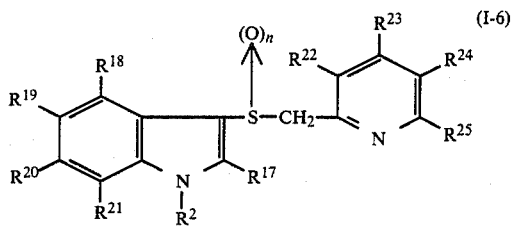

wherein $R^2$ is a hydrogen atom or an alkyl group of 1–6 carbon atoms; $R^{17}$ is a hydrogen atom or an alkyl group of 1–6 carbon atoms; $R^{18}$, $R^{19}$, $R^{20}$ and $R^{21}$ are the same or different and each are a hydrogen atom, a halogen atom, an alkyl group of 1–6 carbon atoms, a trifluoromethyl group, an alkoxy group of 1–6 carbon atoms, an alkanoyl group of 2–6 carbon atoms or an alkoxycarbonyl group of 2–6 carbon atoms; $R^{22}$, $R^{24}$ and $R^{25}$ are the same or different and each are a hydrogen atom or an alkyl group of 1–6 carbon atoms; $R^{23}$ is a group of the formula

where $R^a$ and $R^b$ are each a hydrogen atom or an alkyl group of 1–6 carbon atoms, or $R^a$ and $R^b$ taken together with the adjacent nitrogen atom form a 5-membered or 6-membered heterocyclic group; and n is zero or 1, or a pharmaceutically acceptable salt of said compound.

In the compound of the formula (I-6), it is preferable that $R^2$ is a hydrogen atom or a methyl or ethyl group; $R^{17}$ is a hydrogen atom or a methyl group; $R^{18}$, $R^{20}$ and $R^{21}$ are each a hydrogen atom; $R^{19}$ is a hydrogen atom, a halogen atom, an alkyl group of 1–6 carbon atoms, a trifluoromethyl group, an alkoxy group of 1–6 carbon atoms, an alkanoyl group of 2–6 carbon atoms or an alkoxycarbonyl group of 2–6 carbon atoms; $R^{22}$ and $R^{24}$ are each a hydrogen atom or an alkyl group of 1–6 carbon atoms; $R^{23}$ is an amino group or a mono- or di-($C_1$–$C_6$)alkylamino group or a 5-membered or 6-membered heterocyclic group containing a nitrogen atom together with or without an oxygen atom, a sulfur atom or a further nitrogen atom as the hetero-atom: $R^{25}$ is a hydrogen atom; and n is zero or 1. More preferably, the group $R^{23}$ is a piperidino group, a pyrrolidino group, a morpholino group a thiomorpholino group or a piperazino group or N-methylpiperazino group as the heterocyclic group. The group $R^{23}$ may also be preferably a group of the formula

where $R^a$ and $R^b$ are each an alkyl group of 1–6 carbon atoms.

The seventh preferred group of the compound (I) of this invention includes a compound of the formula (I-7):

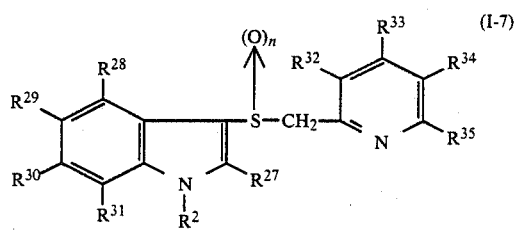

wherein $R^2$ is a hydrogen atom or an alkyl group of 1–6 carbon atoms; $R^{27}$ is a hydrogen atom or an alkyl group of 1–6 carbon atoms; $R^{28}$, $R^{29}$, $R^{30}$ and $R^{31}$ are the same or different and each are a hydrogen atom, a halogen atom, an alkyl group of 1–6 carbon atoms, a trifluoromethyl group, an alkoxy group of 1–6 carbon atoms, an alkanoyl group of 2–6 carbon atoms or an alkoxycarbonyl group of 2–6 carbon atoms; $R^{32}$, $R^{34}$ and $R^{35}$ are the same or different and each are a hydrogen atom or an alkyl group of 1–6 carbon atoms; $R^{33}$ is a halogen atom, a hydroxy group or an alkoxycarbonyl group of 2–6 carbon atoms, and n is zero or 1, or a pharmaceutically acceptable salt of said compound.

In the compound of the formula (I-7), it is preferred that $R^2$ is a hydrogen atom, $R^{27}$, $R^{28}$, $R^{29}$, $R^{30}$, $R^{31}$, $R^{32}$, $R^{34}$ and $R^{35}$ are each a hydrogen atom; and $R^{33}$ is a halogen atom, a hydroxy group or an alkoxycarbonyl group of 2–6 carbon atoms, and n is zero.

In the following are listed particular examples of the new compounds according to the formula (I).

1. 2-[(5-ethyl-4-piperidino-2-pyridyl)methylthio]indole
2. 2-[(5-butyl-4-piperidino-2-pyridyl)methylthio]indole
3. 2-[(5-methyl-4-piperidino-2-pyridyl)methylthio]indole
4. 5-methyl-2-[(5-methyl-4-piperidino-2-pyridyl)methylthio]indole
5. 5-fluoro-2-[(5-methyl-4-piperidino-2-pyridyl)methylthio]indole
6. 2-{[5-methyl-4-(3-methylpiperidino)-2-pyridyl]methylthio}indole
7. 2-{[5-methyl-4-(4-methylpiperidino)-2-pyridyl]methylthio}indole
8. 5-ethyl-2-[(5-methyl-4-dimethylamino-2-pyridyl)methylthio]indole
9. 5-acetyl-2-[(5-methyl-4-piperidino-2-pyridyl)methylthio]indole
10. 5-ethoxycarbonyl-2-[(5-methyl-4-piperidino-2-pyridyl)methylthio]indole
11. 2-[(3-methyl-4-piperidino-2-pyridyl)methylthio]indole
12. 2-[(5-methyl-4-morpholino-2-pyridyl)methylthio]indole
13. 5-ethyl-2-[(5-methyl-4-piperidino-2-pyridyl)methylthio]indole 14. 6-methyl-2-[(4-piperidino-2-pyridyl)methylthio]indole
15. 5,6-dimethyl-2-[(5-methyl-4-piperidino-2-pyridyl)methylthio]indole
16. 2-[(5-methyl-4-pyrrolidino-2-pyridyl)methylthio]indole
17. 2-[(4-dimethylamino-2-pyridyl)methylthio]indole
18. 5-methyl-2-[(4-dimethylamino-2-pyridyl)methylthio]indole
19. 5-methoxy-2-[(4-dimethylamino-2-pyridyl)methylthio]indole
20. 5-fluoro-2-[(4-dimethylamino-2-pyridyl)methylthio]indole
21. 4,7-dimethyl-2-[(4-piperidino-2-pyridyl)methylthio]indole
22. 5-ethoxycarbonyl-6-methyl-2-[(5-methyl-4-piperidino-2-pyridyl)methylthio]indole
23. 5-propoxy-2-[(4-piperidino-2-pyridyl)methylthio]indole
24. 6-acetyl-5-methyl-2-[(3-methyl-4-piperidino-2-pyridyl)methylthio]indole
25. 6-trifluoromethyl-2-[(5-methyl-4-piperidino-2-pyridyl)methylthio]indole
26. 5-trifluoromethyl-2-[(4-dimethylamino-2-pyridyl)methylthio]indole
27. 5-acetyl-2-[(4-dimethylamino-2-pyridyl)methylthio]indole
28. 5-ethoxycarbonyl-2-[(4-dimethylamino-2-pyridyl)methylthio]indole
29. 6,7-dimethyl-2-[(4-dimethylamino-2-pyridyl)methylthio]indole
30. 2-[(4-pyrrolidino-2-pyridyl)methyl]indole
31. 5-methoxy-2-[(5-ethyl-4-pyrrolidino-2-pyridyl)methylthio]indole
32. 5-ethoxycarbonyl-2-[(4-pyrrolidino-2-pyridyl)methylthio]indole
33. 5-methyl-2-[(4-pyrrolidino-2-pyridyl)methylthio]indole
34. 5-trifluoromethyl-2-[(5-methyl-4-piperidino-2-pyridyl)methylthio]indole
35. 2-[(5-methyl-4-thiomorpholino-2-pyridyl)methylthio]indole
36. 2-{[4-(4-methylpiperazino)-2-pyridyl]methylthio}indole
37. 2[(4-piperidino-2-pyridyl)methylthio]indole
38. 5-methoxy-2-[(5-methyl-4-piperidino-2-pyridyl)methylthio]indole
39. 5-fluoro-2-[(3,5-dimethyl-4-methoxy-2-pyridyl)methylthio]indole
40. 2-(2-pyridylmethylthio)-5-methoxyindole
41. 2-(3-pyridylmethylthio)-5-methoxyindole
42. 2-(4-pyridylmethylthio)-5-methoxyindole
43. 2-[(3,5-dimethyl-4-methoxy-2-pyridyl)methylthio]indole
44. 3-methyl-2-[(3,5-dimethyl-4-methoxy-2-pyridyl)methylthio]indole
45. 5-methyl-2-[(3,5-dimethyl-4-methoxy-2-pyridyl)methylthio]indole
46. 5-trifluoromethyl-2-[(3,5-dimethyl-4-methoxy-2-pyridyl)methylthio]indole
47. 5-methoxy-2-[(3,5-dimethyl-4-methoxy-2-pyridyl)methylthio]indole
48. 5-methoxycarbonyl-2-[(3,5-dimethyl-4-methoxy-2-pyridyl)methylthio]indole
49. 5-acetyl-2-[(3,5-dimethyl-4-methoxy-2-pyridyl)methylthio]indole
50. 3-methylthio-2-[(3,5-dimethyl-4-methoxy-2-pyridyl)methylthio]indole
51. 7-trifluoromethyl-2-[(3,5-dimethyl-4-methoxy-2-pyridyl)methylthio]indole
52. 3-[(5-methyl-4-piperidino-2-pyridyl)methylthio]indole
53. 3-[(4-dimethylamino-2-pyridyl)methylthio]indole
54. 3-[(4-piperidino-2-pyridyl)methylthio]indole
55. 3-[(4-chloro-2-pyridyl)methylthio]indole
56. 3-[(4-ethoxycarbonyl-2-pyridyl)methylthio]indole
57. 3-[(4-hydroxy-2-pyridyl)methylthio]indole
58. 3-[(5-methyl-4-pyrrolidino-2-pyridyl)methylthio]indole
59. 3-[(2-pyridyl)methylthio]indole
60. 5-fluoro-3-[(3,5-dimethyl-4-methoxy-2-pyridyl)methylthio]indole
61. 3-[(3,5-dimethyl-4-methoxy-2-pyridyl)methylthio]indole
62. 2-methyl-3-[(3,5-dimethyl-4-methoxy-2-pyridyl)methylthio]indole
63. 5-methoxy-3-[(3,5-dimethyl-4-methoxy-2-pyridyl)methylthio]indole
64. 5-methoxycarbonyl-3-[(3,5-dimethyl-4-methoxy-2-pyridyl)methylthio]indole
65. 2-[(5-ethyl-4-piperidino-2-pyridyl)methylsulfinyl]indole
66. 2-[(5-methyl-4-piperidino-2-pyridyl)methylsulfinyl]indole
67. 2-{[6-methyl-4-(4-methylpiperidino)-2-pyridyl]methylsulfinyl}indole
68. 1-methyl-2-[(5-methyl-4-piperidino-2-pyridyl)methylsulfinyl]indole
69. 2-[(5-methyl-4-pyrrolidino-2-pyridyl)methylsulfinyl]indole
70. 5-fluoro-2-[(3,5-dimethyl-4-methoxy-2-pyridyl)methylsulfinyl]indole
71. 2-(2-pyridylmethylsulfinyl)-5-methoxyindole
72. 2-(3-pyridylmethylsulfinyl)-5-methoxyindole
73. 2-(4-pyridylmethylsulfinyl)-5-methoxyindole
74. 2-[(3,5-dimethyl-4-methoxy-2-pyridyl)methylsulfinyl]indole
75. 3-methyl-2-[(3,5-dimethyl-4-methoxy-2-pyridyl)methylsulfinyl]indole
76. 5-methyl-2-[(3,5-dimethyl-4-methoxy-2-pyridyl)methylsulfinyl]indole
77. 5-trifluoromethyl-2-[(3,5-dimethyl-4-methoxy-2-pyridyl)methylsulfinyl]indole
78. 5-methoxy-2-[(3,5-dimethyl-4-methoxy-2-pyridyl)methylsulfinyl]indole
79. 5-methoxycarbonyl-2-[(3,5-dimethyl-4-methoxy-2-pyridyl)methylsulfinyl]indole
80. 5-acetyl-2-[(3,5-dimethyl-4-methoxy-2-pyridyl)methylsulfinyl]indole
81. 7-trifluoromethyl-2-[(3,5-dimethyl-4-methoxy-2-pyridyl)methylsulfinyl]indole
82. 3-[(3,5-dimethyl-4-methoxy-2-pyridyl)methylsulfinyl]indole
83. 2-methyl-3-[(3,5-dimethyl-4-methoxy-2-pyridyl)methylsulfinyl]indole
84. 5-methoxycarbonyl-3-[(3,5-dimethyl-4-methoxy-2-pyridyl)methysulfinyl]indole
85. 1-methyl-2-[(5-methyl-4-piperidino-2-pyridyl)methylthio]indole
86. 1-ethyl-2-[(4-piperidino-2-pyridyl)methylthio]indole
87. 1-methyl-2-[(5-methyl-4-pyrrolidino-2-pyridyl)methylthio]indole Now, the production of the new compounds of the general formula (I) or a salt thereof according to this invention, is described. Thus, the compound of the formula (I) may be produced by reacting a thiol compound of the formula (II)

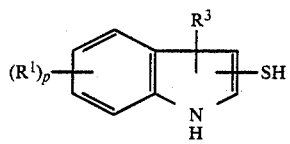  (II)

wherein $R^1$, $R^3$ and p are as defined hereinbefore or a functionally equivalent derivative of said thiol compound with a pyridine compound of the formula (III)

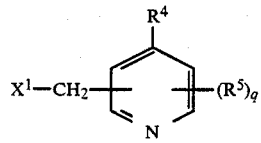  (III)

wherein $R^4$, $R^5$ and q are as defined hereinbefore and $X^1$ is a leaving group, or a salt of said pyridine compound in an organic solvent, either anhydrous or aqueous, to produce a condensation product compound of the formula (Ia)

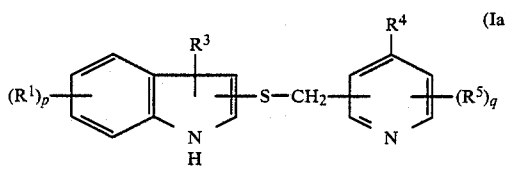  (Ia)

wherein $R^1$, $R^3$, $R^4$, $R^5$, p and q are as defined above, and then, if necessary, subjecting the condensation product compound of the above formula (Ia) to either one or both of the following two steps (a) and (b):

(a) an alkylation step of reacting the compound of the formula (Ia) with a compound of the formula (IV)

$$X^2-R^6 \quad (IV)$$

wherein $R^6$ is a lower alkyl group and $X^2$ is a leaving group, to alkylate the nitrogen atom at the 1-position of the compound of the formula (Ia), and (b) an oxidation step of converting the sulfide form of the compound of the formula (Ia) or the N-alkylated product of the above alkylation step (a) into a corresponding sulfoxide form by oxidation of the thio group present in said compound.

Thus, such compound of the formula (I) where n is 1 and which is of the form of sulfoxide may be produced by oxidizing the thio group of such compound of the formula (I) where n is zero and which is of the form of sulfide and has been prepared by the condensation reaction of the thiol compound of the formula (II) with the pyridine compound of the formula (III).

According to a second aspect of this invention, therefore, there is provided a process for the production of the compound of the formula (I)

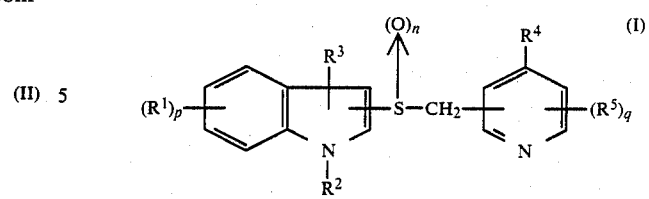  (I)

wherein $R^1$ is a hydrogen atom, a halogen atom, a lower alkyl group, a trifluoromethyl group, a lower alkoxy group, an acyl group or a lower alkoxycarbonyl group; $R^2$ is a hydrogen atom or a lower alkyl group; $R^3$ is a hydrogen atom, a lower alkyl group, a lower alkoxy group or a lower alkylthio group; $R^4$ is a hydrogen atom, a lower alkyl group, a lower alkoxy group, a halogen atom, a hydroxy group, a lower alkoxycarbonyl group, a substituted or unsubstituted aralkyloxy group, or a group of the formula $-NR^aR^b$ where $R^a$ and $R^b$ are the same or different and each are a hydrogen atom or a lower alkyl group, or $R^a$ and $R^b$ taken together with the adjacent nitrogen atom form a 5-membered or 6-membered heterocyclic group containing optionally a further hetero-atom therein; $R^5$ is a hydrogen atom, a lower alkyl group, a lower alkoxy group, an aralkyl group or a substituted or unsubstituted aralkyloxy group; and n is an integer of zero or 1, p is an integer of 1, 2, 3 or 4; and q is an integer of 1, 2 or 3, or a salt of said compound, which comprises reacting a thiol compound of the formula (II)

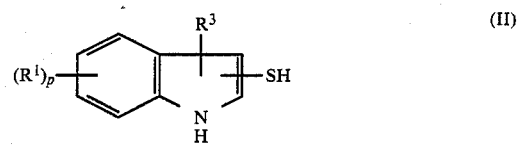  (II)

wherein $R^1$, $R^3$ and p are as defined above, or a functionally equivalent derivative of said thiol compound with a pyridine compound of the formula (III)

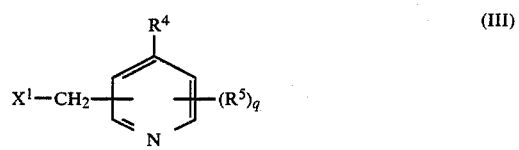  (III)

wherein $R^4$, $R^5$ and q are as defined above or a salt of said pyridine compound to produce the condensation product, and then, if necessary, further subjecting the resulting condensation product compound to at least one of the following two steps (a) and (b):

(a) the step of alkylating the nitrogen atom in the indole ring of said condensation product compound or its sulfoxide derivative with a compound of the formula (IV)

$$X^2-R^6 \quad (IV)$$

wherein $R^6$ is a lower alkyl group equal to that as represented by the group $R^2$ in the compound of the formula (I) where $R^2$ is a lower alkyl group and wherein $X^2$ is a leaving group, and (b) the step of converting the sulfide form of said condensation product compound or of the N-alkylated product compound of the above step (a) into a corresponding sulfoxide by oxidation of the thio group present therein.

The group $X^1$ in the compound of the formula (III) as used in the process of this invention is a leaving group of such nature that it can be liberated with formation of the compound $HX^1$ when the compound (III) is reacted with the compound (II). Similarly, the group $X^2$ in the compound of the formula (IV) is a leaving group of such nature that it can be liberated with formation of the compound $HX^2$ when the compound (IV) is reacted with the indole compound of the formula (Ia) shown hereinbefore. Suitable examples of the leaving groups $X^1$ and $X^2$ may be, for example, a halogen atom such as chlorine, bromine and iodine atoms; an arylsulfonyloxy group such as benzenesulfonyloxy and p-toluenesulfonyloxy groups; and an alkylsulfonyloxy group such as methanesulfonyloxy and ethanesulfonyloxy groups. Suitable example of a functionally equivalent derivative of the thiol compound of the formula (II) may be a salt of said thiol compound, such as an alkali metal salt (mercaptide) such as sodium and potassium salts.

In the process of the second aspect of this invention, the condensation reaction of the compound (II) with the compound (III) may be carried out in a water-miscible organic solvent such as a lower alkanol, especially methanol and ethanol; acetone, tetrahydrofuran, N,N-dimethylformamide, dimethylsulfoxide and the like, or in a mixture of said organic solvent with water at a temperature of 0° C. to 150° C., preferably at a temperature of from ambient temperature to 100° C., and, if desired, in the presence of an acid-binder which may be an inorganic base or an organic base. The base suitable as the acid-binder may be an inorganic base, for example, an alkali metal hydroxide such as sodium hydroxide and potassium hydroxide; an alkali metal (hydrogen) carbonate such as sodium hydrogen carbonate, potassium hydrogen carbonate, sodium carbonate, and potassium carbonate; and an organic base, for example, amines such as a tri-lower-alkylamine, especially triethylamine and pyridine. After completion of the condensation reaction, the reaction solution may be processed in a known manner to recover the desired condensation product compound of this invention therefrom. Isolation and purification of the product compound of this invention may be achieved by ordinary procedures such as extraction with organic solvent, recrystallization and chromatography.

The condensation step of reacting the thiol compound (II) with the pyridine compound (III) gives, as the condensation product, the new compound of this invention of such type shown by the formula (Ia) above.

In the process according to the second aspect of this invention, if necessary, the compound of the formula (Ia) as produced or a salt thereof may further be subjected to the step (a) of reacting said compound (Ia) or a salt thereof with the alkylating agent compound of the formula (IV) to produce a compound of this invention of such type shown by the formula (Ic):

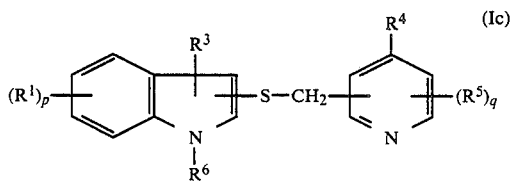

wherein $R^1$, $R^3$, $R^4$, $R^5$, $R^6$, p and q are as defined hereinbefore. This alkylation step (a) of reacting the compound (Ia) or a salt thereof with the alkylating agent compound (IV) may be carried out in the same manner as for the step of reaction of the compound (II) with the compound (III) and thus at a temperature of 0° C. to 150° C. in an a water-miscible organic solvent or a mixture of such organic solvent with water and, if desired, in the presence of an acid-binder which may be the inorganic or organic bases mentioned hereinbefore.

Besides, in the process of the second aspect invention, the compound of the formula (Ia) (in the sulfide form) as produced or a salt thereof may, if necessary, be further subjected to the oxidation step (b) of converting the compound (Ia) or a salt thereof into its sulfoxide derivative of the formula (Ib):

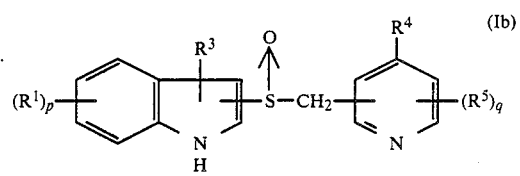

wherein $R^1$, $R^3$, $R^4$, $R^5$, p and q are as defined above or a salt thereof.

Furthermore, in the process of the second aspect invention, the compound of the formula (Ia) (in the sulfide form) as produced or a salt thereof may, if necessary, be further subjected to the alkylation step (a) of reacting the compound (Ia) with the alkylation agent (IV) and also to the oxidation step (b) of converting the resulting N-alkylated product compound of the step (a) into the sulfoxide type of the compound represented by the formula (Id):

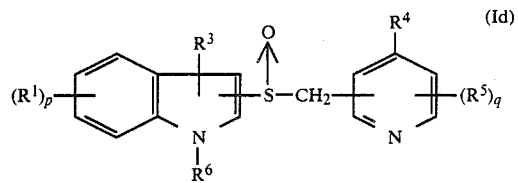

wherein $R^1$, $R^3$, $R^4$, $R^5$, $R^6$, p and q are as defined hereinbefore, or a salt thereof.

The above-mentioned oxidation step (b) of converting the compound of the formula (Ia) or the compound of the formula (Ic) (in the sulfide form) into the corresponding sulfoxide compound of the formula (Ib) or (Id) may be carried out by reacting the compound (Ia) or (Ic) with an oxidizing agent at a temperature of −30° C. to 60° C., preferably at a temperature of from 0° C. to 10° C. in such a reaction medium which may be water or a water-miscible organic solvent such as a lower alkanol, especially methanol and ethanol, and acetic acid, or a water-immiscible organic solvent such as benzene, methylene chloride, chloroform and the like or mixed solvents of two or more of said solvents. The oxidizing agent available in this oxidation step may be such an oxidizing compound which has usually been employed for the oxidation of sulfides into sulfoxides. Suitable examples of the available oxidizing agent include hydrogen peroxide, peracetic acid, m-chloroperbenzoic acid, sodium metaperiodate and the like. The oxidizing agent may preferably be used in a proportion of 1 to 1.2 equivalents per equivalent of the compound (Ia) or (Ic). After completion of the oxidation reaction, the reaction mixture may be processed in a known manner to recover the desired sulfoxide derivative of the formula (Ib) or (Id). Isolation and purification of the compound (Ib) or (Id) may be performed by ordinary procedures such as organic solvent extraction, recrystallization, and chromatography.

In the process of the second aspect invention, if desired, the oxidation step (b) may preceed the alkylation step (a), and in other words, the oxidation step (b) may be carried out with the condensation product compound of the formula (Ia) to oxidize the thio group (—S—) present therein into the sulfoxide group

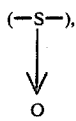

before the indole ring nitrogen atom in the sulfoxide derivative of the formula (Ib) as produced is alkylated with the alkylating agent (IV) in the alkylation step (a).

The thiol compound of the formula (II) which is used as a starting compound in the process of the second aspect of this invention may be prepared by the following methods. For instance, a 2-mercaptoindole compound of the formula (IIa)

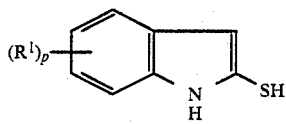

which is covered by the compound of the general formula (II) and in which $R^1$ and p have the same meanings as above may be prepared by such a method comprising producing 2-oxiindoles from an aniline compound according to the process of P. G. Gassman et al (see "J. Am. Chem. Soc." 95, 2718 (1973); ditto 96, 5508 (1974)) and then reacting the 2-oxiindoles e.g. with phosphorus pentasulfide in an organic solvent such as benzene, toluene, pyridine and tetrahydrofuran at a temperature of 20° C. to 100° C. When the reaction of the 2-oxiindoles with phosphorus pentasulfide is conducted in a neutral organic solvent, the reaction may preferably be carried out in the presence of an appropriate base such as triethylamine in order to promote the reaction.

A starting 3-mercaptoindole compound of the formula (IIb)

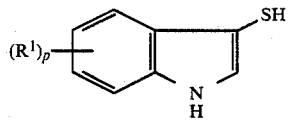

which is also covered by the compound of the general formula (II) and in which $R^1$ and p have the same meanings as above may be prepared by such a method comprising producing an indole compound from an aniline compound according to the process of P. G. Gassman et al (see "J. Am. Chem. Soc." 96, 5495 (1974)) and then treating the resulting indole product with the process of R. L. N. Harrison et al. (see "Tetrahedron Letters" page 4465 (1965)), or alternatively by such a method comprising reacting a 3-halogeno-indole with thiourea and then reacting the resulting isothiuronium salt with an alkali metal hydroxide or sodium sulfide.

If desired, the starting compound (II) may be prepared by an appropriate synthetic method in situ in the reaction medium in which the reaction of the compound (II) with the compound (III) is to be effected according to the process of this invention, and the compound (II) as thus prepared may directly be used for the subsequent reaction with the compound (III), without being previously isolated and purified. For instance, a starting 3-mercapto-indole compound according to the formula (II) may be prepared in situ by reacting an S-(3-indolyl)-isothiuronium halide of the formula (IIc)

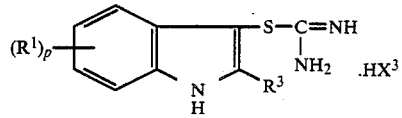

wherein $R^1$, $R^3$ and p are as defined hereinbefore and $X^3$ is a halogen atom such as iodine, bromine or chlorine atom, in ethanol with aqueous sodium hydroxide.

Pharmacological Activities

The inhibitory effects of the new compound of this invention on the gastric acid secretion and the cytoprotective effects of the new compound of this invention on the gastric mucosa have been estimated by the following pharmacological tests.

TEST 1

Inhibitory Effects on Aminopyrine Uptake into Gastric Glands

The production of gastric acid in the gastric mucosa is known to be performed by the parietal cells which are one kind of the cells constituting the gastric glands. The extent of the gastric acid secretion by the parietal cells has been deduced to be proportional to the rate of aminopyrine uptake into the gastric glands. Accordingly, the investigation of aminopyrine uptake into the gastric glands has been generally used as the indirect method for measuring the gastric acid secretion. Therefore, suspension of the rabbit gastric glands was prepared according to the method of Berglindh et al (see "Acta Physiol. Scand." 97, 401–414 (1976)). A mixture of the gastric gland suspension (1 ml) and 0.05 µCi $^{14}C$-aminopyrine (specific radio-activity of 103.2 mCi/m mol) was incubated at 37° C. for 30 minutes in the presence of 10 µl of methanol. After this incubation, the reaction mixture obtained was centrifuged so that the gastric glands were spun down and separated from the incubation mixture. The gastric glands so collected were liophylized and the dry weight of the glands was measured. The dried gastric glands were then solubilized with aqueous 0.5N sodium hydroxide and then admixed with a toluene-Triton scintillator, and the radio-activity was determined by the liquid scintillation counter (Packard 460 CD-model). The so determined value of the radio-activity was assumed as the concentration or level of the aminopyrine uptaken into the gastric glands. According to the report of Berglindh et al (see "Acta Physiol. Scand." 96, 150–159 (1976)), it was assumed that the volume of the intraglandular water was amounting to a value of 2 times as much as the dry weight of the gastric glands. The radio-activity of the supernatant of the incubation mixture was determined in the same manner as above by the liquid scintillation counter, and the so determined value of the radioactivity of the supernatant was assumed to be the concentration or level of the aminopyrine present in the extraglandular water with the assumption that the so determined concentration of the aminopyrine in the supernatant was a measure of showing the quantity of the aminopyrine remaining not uptaken into gastric glands. Rate of aminopyrine uptake into gastric glands was calculated according to the following equation:

$$\text{Rate of aminopyrine uptake} = \frac{\text{(aminopyrine in intraglandular water)}}{\text{(aminopyrine in extraglandular water)}} \times 100$$

The above experiment was repeated without the test compound as the Control test (untreated with test compound), and the rate of aminopyrine uptake as determined for this control test (untreated) was assumed to be 100%. The value (% of Control) was taken as showing the inhibitory effects of the test compound on the acid secretion. The estimated values (as % of Control) of the test compounds for the aminopyrine uptake rate are shown in Table 1 below.

As a comparative drug, omeprazole was tested in the same way as above.

TABLE 1

| Test Compound | Aminopyrine uptake (% of Control) Concentration (M) of test compound* | | |
|---|---|---|---|
| | $10^{-6}$ | $10^{-5}$ | $10^{-4}$ |
| Example 1 Compound | 44 | 14 | 7 |
| Example 2 Compound | 111 | 72 | 24 |
| Example 3 Compound | 99 | 64 | 54 |
| Example 4 Compound | 50 | 8 | 7 |
| Example 5 Compound | 56 | 18 | 11 |
| Example 6 Compound | 48 | 76 | 14 |
| Example 7 Compound | 55 | 17 | 14 |
| Example 9 Compound | 61 | 20 | 15 |
| Example 10 Compound | 71 | 19 | 4 |
| Example 11 Compound | 106 | 56 | 3 |
| Example 12 Compound | 48 | 11 | 10 |
| Example 13 Compound | 118 | 48 | 3 |
| Example 37 Compound | 114 | 105 | 95 |
| Example 38 Compound | 120 | 103 | 141 |
| Example 39 Compound | 120 | 109 | 105 |
| Omeprazole (comparative) | 34 | 25 | 18 |

*This concentration (M) shows the final concentration of the test compound in the incubation mixture.

From the results of Table 1, it is clear that the compounds of this invention exhibit the inhibitory effects on the aminopyrine uptake into the gastric glands and thus exhibit the inhibitory effects on the gastric acid secretion.

The identification of the tested compounds are as follows:

Example 1 Compound: 2-[(5-methyl-4-piperidino-2-pyridyl)methylthio]indole
Example 2 Compound: 3-[(4-dimethylamino-2-pyridyl)methylthio]indole
Example 3 Compound: 2-[(5-methyl-4-piperidino-2-pyridyl)methylsulfinyl]indole
Example 4 Compound: 1-methyl-2-[(5-methyl-4-piperidino-2-pyridyl)methylthio]indole
Example 5 Compound: 5-methyl-2-[(5-methyl-4-piperidino-2-pyridyl)methylthio]indole
Example 6 Compound: 5-fluoro-2-[(5-methyl-4-piperidino-2-pyridyl)methylthio]indole
Example 7 Compound: 5-trifluoromethyl-2-[(5-methyl-4-piperidino-2-pyridyl)methylthio]indole
Example 9 Compound: 5-ethoxycarbonyl-2-[(5-methyl-4-piperidino-2-pyridyl)methylthio]indole
Example 10 Compound: 2-[(3-methyl-4-piperidino-2-pyridyl)methylthio]indole
Example 11 Compound: 2-[(5-methyl-4-morpholino-2-pyridyl)methylthio]indole
Example 12 Compound: 2-[(5-methyl-4-pyrrolidino-2-pyridyl)methylthio]indole
Example 13 Compound: 2-[(4-dimethylamido-2-pyridyl)methylthio]indole
Example 37 Compound: 3-[(4-chloro-2-pyridyl)methylthio]indole
Example 38 Compound: 3-[(4-ethoxycarbonyl-2-pyridyl)methylthio]indole
Example 39 Compound: 3-[(4-hydroxy-2-pyridyl)methylthio]indole
Omeprazole: 2-[(3,5-dimethyl-4-methoxy-2-pyridyl)methylsulfinyl]-5-methoxybenzimidazole.

TEST 2

Inhibitory Effects on the Enzymatic Activity of H+,K+-ATPase

The rabbit gastric glands were homogenized and the microsomal fractions were prepared by differential centrifugation of the resultant homogenate. The microsomal fractions were layered on a linear continuous sucrose gradient ranging from 20 to 55% (W/V) sucrose and centrifuged to obtain the light membrane fractions sedimenting between 30% sucrose and 40% sucrose. The light membrane fractions containing the H+,K+-ATPase so obtained were used to estimate the inhibitory effects of the new compound of this invention or omeprazole on the enzymatic activity of H+,K+-ATPase. Test compounds were pre-incubated with the reaction mixture containing the enzyme (20–50 μg as protein) for 30 minutes at 37° C. After this, the enzymatic activity of the reaction mixture was determined by incubating for 20 minutes at 37° C. with the following reactant mixture comprising 10 mM MgCl₂, 10 mM ATP disodium salt and 400 mM Tris-HCl (pH 7.3) with or without 50 mM KCl. From the results obtained, for instance, it was seen that the IC₅₀ value of the Example 1 Compound of this invention required for 50% inhibition of the enzymatic activity was $5 \times 10^{-5}$M and the IC₅₀ value of the Example 13 Compound of this invention was $7 \times 10^{-4}$M, whereas the IC₅₀ value of omeprazole (as a comparator) was $9.4 \times 10^{-6}$M. These results have revealed that the test compounds, Examples 1 and 13 of this invention, are H+,K+-ATPase inhibitors.

TEST 3

Effects of Preventing the Gastric Ulcer Induced by Ethanol-Hydrochloric Acid

It is known that some prostaglandins possess the remarkable and unique property of protecting the gastric mucosa against damaging agents (for exampoe, ethanol and/or hydrochloric acid), and this phenomenon has been called "cytoprotection". It is also known that prostaglandins exhibit the cytoprotective effect even at the nonantisecretory doses, so that the cytoprotection seems to be independent of the gastric acid inhibition.

The following test were made to demonstrate that the new compound of this invention exhibits the effects of the gastric cytoprotection, namely the effects of preventing the gastric ulcer induced by oral administration of ethanol-hydrochloric acid. Thus, according to the method of Robert et al (see "Gastroenterology" 77, 433-443 (1979)), SD-strain rats (male, weighing 200 to 220 g, 8 rats in each group) were deprived of food for 24 hours and deprived of water for 19 hours. The rats were then administered orally with a suspension of the test compound in aqueous 0.5% carboxymethylcellulose solution at a dosage of 6, 10 or 20 mg/kg of the test compound.

30 minutes later than the administration of the test compound, 1 ml of 0.2N hydrochloric acid-50% aqueous ethanol per rat was orally given to the rats. One hour after the administration of the ethanolic hydrochloric acid, the rats were killed. Their stomacks were dissected out, and the lower part of the esophagus was nipped with a clip. Aqueous 1% formalin solution (12.0 ml) was poured into the stomacks from duodenum and then the duodenal part was nipped by a clip. The whole stomacks were immersed in aqueous 1% formalin solution for about 10 minutes for the fixation, the pyloric stomacks were opened along the greater curvature and then rinsed with water. The gastric mucosa was examined and the necrotic lesions or errosions as formed in the glandular stomach and in the pylorus were examined under anatomic microscope to determine the length (in mm) of the lesions.

From the test results obtained by the above procedure, the $ED_{50}$ value of the tested compound effective for 50% inhibition to the formation of necrotic lesions was evaluated. The $ED_{50}$ data so obtained are shown in Table 2 below.

Omeprazole as the comparative drug was tested in the same manner as above.

TABLE 2

| Test Compound | $ED_{50}$ (mg/kg, p.o.) |
| --- | --- |
| Example 1 Compound | 11.54 |
| Example 5 Compound | 8.59 |
| Example 6 Compound | 12.65 |
| Example 7 Compound | 9.77 |
| Example 13 Compound | 9.17 |
| Example 21 Compound | 14.60 |
| Example 22 Compound | 8.13 |
| Example 40 Compound | 2.84 |
| Omeprazole (comparative) | 34.06 |

From the test results of the above table, it is clear that the effective dose of the compound of this invention for 50% inhibition ($ED_{50}$) to the necrotic lesions is remarkably superior to the $ED_{50}$ value of omeprazole in respect of their effects of preventing the gastic ulcer induced by the ethanolic hydrochloric acid and thus in respect of their gastric cytoprotective effects.

Identification of the tested compounds of Examples 21, 22 and 40 according to this invention are as follows:

Example 21 Compound: 5-methoxy-2-[(5-methyl-4-piperidino-2-pyridyl)methylthio]indole Example 22 Compound: 2-[(4-piperidino-2-pyridyl)methylthio]indole Example 40 Compound: 3-[(5-methyl-4-piperidino-2-pyridyl)methylthio]indole.

TEST 4

Gastric Acid Antisecretory Activity

Donryu-strain rats (male, weighing 210-240 g) were deprived of food for 24 hours and then anaesthetized by intraperitoneal injection of 1.2 g/kg of urethane. The bilateral vagus nerves in the cervical region of the rats were surgically cut and cannulas were inserted into the pylorus and also into the esophagus, respectively, and tied in place according to the method of Ghosh and Schild (see "Brit. J. Pharmacol." 13, 54 (1958)). Aqueous 0.9% saline solution (pH 8.5) as warmed to 40° C. was passed through the esphagal cannula into the stomack at a rate of 1 ml/min. for the perfusion. The pH value of the effluent coming from the pyloral cannula was measured. At the stage when the pH value of said effluent became steady, 5 μg/kg of tetragastrin, a stimulant for the gastric acid secretion, was administered through a cannula which had been inserted into the cervical vein. After the administration of tetragastrin, the decreasing change of pH value in the effluent was measured at constant intervals of time. Subsequently, a solution of the test compound in methanol was intravenously administered to the rat, and 15 minutes later tetragastrin was again administered.

From the test data of the pH measurements so obtained was evaluated the $ED_{50}$ value of the tested compound effective for 50% inhibition of the gastric acid secretion. The $ED_{50}$ data of the tested compounds are shown in Table 3 below.

TABLE 3

| Test Compound | $ED_{50}$ (mg/kg, i.v.) |
| --- | --- |
| Example 1 Compound | 7.58 |
| Omeprazole (comparative) | 0.24 |

From the $ED_{50}$ data of the above Table 3, it is clear that the new compound of this invention represented by the tested Example 1 Compound has a higher $ED_{50}$ value than that of the comparative omeprazole for the effective dose for 50% inhibition to the gastric acid secretion, revealing that the gastric acid antisecretory activity of the new compound of this invention is remarkedly milder than that of opeprazole.

Thus, the results of the above Tests 1-4 have demonstrated that the compound of this invention exhibits a mild inhibitory activity to the gastric acid secretion and a remarkably high cytoprotective activity on the gastric mucosa, in combination.

The new compound of this invention is administrable as an antiulcer agent to mammalian animals and humans for the therapeutic treatment of gastric ulcers. The compound of this invention may be administered orally or non-orally, for instance, intramuscularly, intrasubcutaneously, intrarectally or intracutaneously. Oral administration is preferred. When used as the antiulcer agent, the compound of this invention may be formulated into various forms suitable for oral or non-oral administration. For example, the compound of this invention may be formulated into a pharmaceutical composition by mixing with one or more of the solid or liquid carrier (excipient), binder, lubricant, disintegrator, antiseptic agent, isotonic additives, stabilizer, dispersing agent, anti-oxidant, coloring agent, favoring agent and buffering agent which are usually employed for the formulation of the antiulcer drugs. The pharmaceutical composition so formulated may be in the form of a solid form such as tablet, hard capsule, soft capsule, granules, powder, fine powder, pills and troach and the like; and in a semi-solid form such as suppository and ointment, as well as in a liquid form such as injectable solution or suspension, emulsion, syrup and the like.

Suitable examples of the additives which may be incorporated into the pharmaceutical composition comprising the compound of this invention as the active ingredient include lactose, fructose, glucose, starch, gelatin, magnesium carbonate, magnesium aluminum metasilicate, synthetic aluminum silicate, silica, talc, magnesium stearate, methylcellulose, carboxymethylcellulose or a salt thereof, arabic gum, polyethylene glycol, p-hydroxybenzoic acid alkyl esters, sugar syrup, ethanol, propylene glycol, vaseline, carbowax, glycerine, sodium chloride, sodium sulfite, sodium phosphate, citric acid and others.

The proportion of the compound of this invention in the pharmaceutical composition may vary depending on the type of the formulation and may usually be in the range of 5% to 100% by weight of the formulation when the formulation is in the state of a solid or a semisolid. The compound of this invention may be incorporated at a concentration of 0.1 to 10% by weight in the liquid formulations. The dosage of the compound of this invention may vary, depending on the nature of the mammalian animals (including humans) to be treated, the route of administration and conditions of the disease and other factors, but the compound of this invention may normally be administered at a dosage of 0.01 to 20 mg/kg a day for an adult person for a general guideline. Of course, the dosage of the compound may be changed according to the conditions of the diseases and the judgement of the doctors. The above dosage may be given at one time or separately at several times a day.

According to the third aspect of this invention, therefore, there is provided a pharmaceutical composition comprising a compound of the formula (I) or a pharmaceutically acceptable salt thereof as the active ingredient in a therepeutically effective amount, in association with a pharmaceutically acceptable carrier for the active ingredient. This pharmaceutical composition may be particularly for use in the treatment for inhibiting the gastric acid secretion and effecting the gastric cytoprotection in a mammalian animal, including human, and the compound of this invention in said composition may be present in a therapeutically effective amount to inhibit the gastric acid secretion and to effect the gastric cytoprotection in the mammalian animal.

According to a further aspect of this invention, there is provided a method for inhibiting the gastric acid secretion and effecting the gastric cytoprotection in a mammalian animal, including human, which comprises administering to the animal suffering from the gastric acid secretion disturbances and the gastrointestinal ulcer a compound of the formula (I) as defined above or a pharmaceutically acceptable salt of said compound in an amount effective to inhibit the gastric acid secretion and effect the gastric cytoprotection in the gastrointestines.

According to another aspect of this invention, there is provided a method for the treatment or prevention of gastrointestinal ulcer in a mammalian animal, including human, suffering from or susceptible to the development of the ulcer, which comprises administering to the animal a compound of the formula (I) as defined above or a pharmaceutically acceptable salt of said compound in an amount effective to therapeutically treat or prevent the ulcer.

The following Examples illustrate the preparation of typical compounds according to this invention.

EXAMPLE 1

Preparation of 2-[(5-methyl-4-piperidino-2-pyridyl)methylthio]indole

To a solution of 2-mercaptoindole (1.34 g, 8.98 mmol) and 2-chloromethyl-5-methyl-4-piperidinopyridine hydrochloride (2.35 g, 9.00 mmol) in ethanol (90 ml) was added a 2N aqueous sodium hydroxide solution (9.0 ml) under ice-cooling, and the mixture was stirred at room temperature for 30 minutes. After the removal of the organic solvent by evaporation under a reduced pressure, a saturated sodium chloride solution was added to the residue and the mixture was extracted with chloroform. The chloroform layer separated was dried over anhydrous magnesium sulfate and then concentrated in vacuo. The residue was purified by a silica gel column chromatography [eluent: chloroform and then chloroform-methanol (50:1)] whereby to yield the titled compound (2.51 g) as a crystalline substance.

Yield: 83%. m.p.: 138°–139° C.

IR (KBr, cm$^{-1}$): 2930, 2800, 1600, 1440, 1420, 1400, 1380, 1350, 1240, 1230, 755, 740.

NMR (DMSO-d$_6$, ppm): 1.30–1.90 (6H, m), 2.17 (3H, s), 2.60–3.00 (4H, m), 3.99 (2H, s), 6.48 (2H, s), 6.80–7.60 (4H, m), 8.20 (1H, s), 10.80 (1H, br.s).

EXAMPLE 2

Preparation of 3-[(4-dimethylamino-2-pyridyl)methylthio]indole

To a solution of S-(3-indolyl)isothioronium iodide (180 mg, 0.75 mmol) of the formula

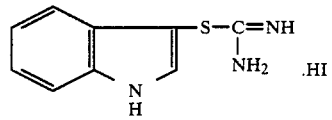

in ethanol (5 ml) was added a 2N aqueous sodium hydroxide solution (0.86 ml) under ice-cooling, and the mixture obtained was stirred at room temperature for 1 hour. The resultant reaction solution containing 3-mercapto-indole so formed was then admixed with 2-chloromethyl-4-dimethylaminopyridine hydrochloride (118 mg, 0.75 mmol), followed by stirring the mixture at room temperature for 1 hour. The resulting reaction was made strongly alkaline with a 2N aqueous sodium hydroxide solution (1.0 ml) and then diluted with water (20 ml) to precipitate crystals, affording the titled compound (130 mg) after filtration.

Yield: 47%, m.p. 189°–191° C.

IR (KBr, cm$^{-1}$): 1610, 1520, 1430, 1380, 1230, 1010, 820, 750.

NMR (DMSO-d$_6$, ppm): 2.70 (6H, s), 3.74 (2H, s), 6.10 (1H, d, J=2 Hz), 6.30 (1H, dd, J=2.7 Hz), 6.85–7.50 (5H, m), 7.90 (1H, d, J=6 Hz), 11.20 (1H, br, s).

EXAMPLE 3

Preparation of 2-[(5-methyl-4-piperidino-2-pyridyl)methylsulfinyl]indole

To a solution of 2-[(5-methyl-4-piperidino-2-pyridyl)-methylthio]indole (80 mg, 0.24 mmol) in chloroform (2.4 ml) was added m-chloroperbenzoic acid (60 mg, 0.35 mmol) under ice-cooling, and the mixture was stirred at that temperature for further 30 minutes. The reaction solution was diluted with chloroform (10 ml) and then washed with a 1% aqueous sodium hydrogen carbonate solution (2.5 ml) and then with a saturated aqueous sodium chloride solution (1 ml). The resulting chloroform layer was dried over anhydrous magnesium sulfate and then concentrated in vacuo. Ethylether (20 ml) was added to the resulting concentration residue to precipitate crystals. After filtration, the titled compound (68 mg) was obtained. Yield: 81%, m.p.: 178° C.

IR (KBr, cm$^{-1}$): 2950, 1595, 1235, 1020, 1010, 985, 815, 745.

NMR (DMSO-d$_6$, ppm): 1.10–1.70 (6H, m), 2.08 (3H, s), 2.20–2.70 (4H, m), 4.48 (1H, d, J=12 Hz), 4.78 (1H, d, J=12 Hz), 6.18 (1H, s), 6.68 (1H, br.s), 6.90–7.70 (4H, m), 8.09 (1H, s).

EXAMPLE 4

Preparation of 1-methyl-2-[(5-methyl-4-piperidino-2-pyridyl)methylthio]indole 2-[(5-Methyl-4-piperidino-2-pyridyl)methylthio]indole (80 mg, 0.24 mmol) was added to a suspension of potassium hydroxide (finely ground) (62 mg) in dimethylsulfoxide (0.5 ml), and the mixture was stirred for 30 minutes. Methyl iodide (34 mg, 0.24 mmol) was then added to the mixture and the stirring was continued at room temperature for further 30 minutes. Then, water (20 ml) was added to the reaction solution and the mixture was extracted with ethyl ether. The ether layer so separated was washed with water, dried over magnesium sulfate and concentrated in vacuo. The residue was purified by a silica gel column chromatography (eluent: chloroform), yielding the titled compound (75 mg) as an oil. Yield: 90%.

IR (CHCl$_3$ solution, cm$^{-1}$): 2940, 1590, 1460, 1450, 1325, 750.

NMR (CDCl$_3$, ppm): 1.20–1.80 (6H, m), 2.12 (3H, s), 2.30–2.70 (4H, m), 3.44 (3H, s), 3.89 (2H, s), 6.07 (1H, s), 6.60 (1H, s), 6.80–7.60 (4 H, m), 8.09 (1H, s).

EXAMPLES 5–36

The following compounds of Examples Nos. (5) to (36) were prepared in the same manner as that described in Example 1.

(5) 5-Methyl-2-[(5-methyl-4-piperidino-2-pyridyl)methylthio]indole m.p. 129°–132° C.

IR (KBr, cm$_{-1}$): 2950, 2800, 1600, 1500, 1450, 1260, 1240, 1180, 1050, 800.

NMR (CDCl$_3$, ppm): 1.60 (6H, m), 2.20 (3H, s), 2.40 (3H, s), 2.80–3.10(4H, m), 4.00(2H, s), 6.42(1H, s), 6.50(1H, s), 6.90(1H, dd, J=2, 10 Hz), 7.20(1H, d, J=10 Hz), 7.21(1H, s), 8.24 (1H, s), 10.50(1H, s).

(6) 5-Fluoro-2-[(5-methyl-4-piperidino-2-pyridyl)methylthio]indole m.p. 136°–137° C.

IR (KBr, cm$^{-1}$): 2950, 2850, 1600, 1500, 1440, 1260, 1150, 870, 800.

NMR (CDCl$_3$, ppm): 1.50–1.90(6H, m), 2.28(3H, s), 2.70–3.10(4H, m), 4.06(2H, s), 6.48(1H, s), 6.80(1H, d, J=7 Hz), 7.10(1H, d, J=7 Hz), 7.24(1H, s), 8.26(1H, s), 11.35(1H, br.s).

(7) 5-Trifluoromethyl-2-[(5-methyl-4-piperidino-2-pyridyl)methylthio]indole m.p. 103°–104° C.

IR (KBr, cm$^{-1}$): 2950, 2850, 1600, 1460, 1340, 1280, 1160, 1120, 1060, 850.

NMR (CDCl$_3$, ppm): 1.40–1.90(6H, m), 2.23(3H, m), 2.70–3.10(4H, m), 4.05(2H, s), 6.55(1H, s), 6.60(1H, s), 7.34(2H, s), 7.74(1H, s), 8.25(1H, s).

(8) 5-Acetyl-2-[(5-methyl-4-piperidino-2-pyridyl)methylthio]indole m.p. 136°–137° C.

IR (KBr, cm$^{-1}$): 2950, 2800, 1670, 1600, 1550, 1350, 1050, 820.

NMR (CDCl$_3$, ppm): 1.50–1.90(6H, m), 2.24(3H, s), 2.62(3H, s), 2.75–3.10(4H, m), 4.07(2H, s), 6.58(1H, s), 6.61(1H, s), 7.31(1H, d, J=10 Hz), 7.80(1H, dd, J=2, 10 Hz), 8.13(1H, d, J=1 Hz), 8.28(1H, s), 12.05(1H, br.s).

(9) 5-Ethoxycarbonyl-2-[(5-methyl-4-piperidino-2-pyridyl)methylthio]indole m.p. 153°–154° C.

IR (KBr, cm$^{-1}$): 2950, 2850, 1700, 1600, 1520, 1460, 1320, 1280, 1000, 780.

NMR (CDCl$_3$, ppm): 1.44(3H, t, J=7 Hz), 1.05–2.00(6H, m), 2.26(3H, s), 2.70–3.20(4H, m), 4.08(2H, s), 4.40(2H, q, J=7 Hz), 6.58(1H, s), 6.63(1H, s), 7.34(1H, d, J=9 Hz), 7.86(1H, dd, J=2, 9 Hz), 8.28(2H, s), 11.85(1H, br.s).

(10) 2-[(3-Methyl-4-piperidino-2-pyridyl)methylthio]indole m.p. 134°–137° C.

IR (KBr, cm$^{-1}$): 2950, 1600, 1460, 1450, 1400, 1360, 1265.

NMR (CDCl$_3$, ppm): 1.40–1.90(6H, m), 2.14(3H, s), 2.60–3.00(4H, m), 4.16(2H, m), 6.46(1H, m), 6.67(1H, d, J=6 Hz), 6.80–7.60(4H, m), 8.25(1H, d, J=6 Hz), 10.60(1H, br.s).

(11) 2-[(5-Methyl-4-morpholino-2-pyridyl)methylthio]indole m.p. 142°–143° C.

IR (KBr, cm$^{-1}$): 2830, 1600, 1260, 1125, 990.

NMR (CDCl$_3$, ppm): 2.19(3H, s), 2.70–3.00(4H, m), 3.60–3.90(4H, m), 4.02(2H, s), 6.46(1H, s), 6.48(1H, s), 6.80–7.60(4H, m), 8.25(1H, s), 10.6(1H, br.s).

(12) 2-[(5-Methyl-4-pyrrolidino-2-pyridyl)methylthio]indole m.p. 179°–180° C.

IR (KBr, cm$^{-1}$): 3060, 2950, 1610, 1540, 1510, 1360, 1330, 1150, 1035, 850, 760.

NMR (CDCl$_3$, ppm): 1.75–2.10(4H, m), 2.38(3H, s), 3.15–3.60(4H, m), 4.04(2H, s), 6.27(1H, s), 6.53(1H, s), 6.90–7.70(4H,s), 8.06(1H,s), 11.45(1H,br.s).

(13) 2-[(4-Dimethylamino-2-pyridyl)methylthio]indole m.p. 128°–129° C.

IR (KBr, cm$^{-1}$): 2900, 1620, 1400, 1360, 1240, 1100, 830, 770.

NMR (DMSO-d$_6$, ppm): 2.76(6H, s), 4.05(2H, s), 6.35(3H, d, J=1 Hz), 6.80–7.50(4H, m), 7.98(1H, d, J=7 Hz), 11.55(1H, br.s).

(14) 5-Methyl-2-[(4-dimethylamino-2-pyridyl)methylthio]indole m.p 109°–112° C.

IR (KBr, cm$^{-1}$): 2920, 1615, 1520, 1440, 1390, 1240, 1220, 1015, 820, 805.

NMR (CDCl$_3$, ppm): 2.37(3H, s), 2.82(6H, s), 3.99(2H, s), 6.20–6.50(3H, m), 6.86(1H, dd, J=2, 9 Hz), 7.10–7.30(2H, m), 8.00–8.30(1H, m), 11.30(1H, br.s).

(15) 2-[(4-Dimethylamino-2-pyridyl)methylthio]-5-methoxyindole
m.p. 108°–110° C.
IR (KBr, cm$^{-1}$): 2930, 1615, 1440, 1420, 1390, 1240, 1170, 1015, 810.
NMR (CDCl$_3$, ppm): 2.80(6H, s), 3.76(3H, s), 3.97(2H, s), 6.10–6.50(3H, m), 6.60–7.20(3H, m), 8.00–8.30(1H, m), 11.30(1H, br.s).

(16) 5-Fluoro-2-[(4-dimethylamino-2-pyridyl)methylthio]indole
m.p. 146°–148° C.
IR (KBr, cm$^{-1}$): 2950, 1620, 1460, 1445, 1290, 1185, 1140, 1115, 1065, 1010, 905, 815.
NMR (CDCl$_3$, ppm): 2.83(6H, s), 3.96(2H, s), 6.20–6.50(3H, m), 6.60–7.30(3H, m), 8.00–8.30(1H, m), 11.90(1H, br.s).

(17) 5-Trifluoromethyl-2-[(4-dimethylamino-2-pyridyl)methylthio]indole
m.p. 178°–180° C.
IR (KBr, cm$^{-1}$): 2400, 1605, 1520, 1455, 1440, 1385, 1160, 1110, 1015, 850, 765.
NMR (CDCl$_3$, ppm): 2.75(6H, s), 3.99(2H, s), 6.13(1H, d, J=3 Hz), 6.36(1H, dd, J=3, 6 Hz), 6.46(1H, s), 7.30–7.50(2H, m), 7.70–7.80(1H, m), 7.93(1H, d, J=6 Hz).

(18) 5-Acetyl-2-[(4-dimethylamino-2-pyridyl)methylthio]indole
m.p. 136°–138° C.
IR (KBr, cm$^{-1}$): 2930, 1660, 1605, 1515, 1365, 1350, 1315, 1265, 1010, 805.
NMR (CDCl$_3$, ppm): 2.69(3H, s), 2.93(6H, s), 4.00(2H, s), 6.30–6.50(2H, m), 6.55(1H, s), 7.31(1H, d, J=9 Hz), 7.73(1H, dd, J=1, 9 Hz), 8.10–8.40(2H, m), 12.60(1H, br.s).

(19) 5-Ethoxycarbonyl-2-[(4-dimethylamino-2-pyridyl)methylthio]indole
m.p. 113°–116° C.
IR (KBr, cm$^{-1}$): 2900, 1705, 1610, 1350, 1315, 1300, 1265, 1240, 1200, 1010, 775.
NMR (CDCl$_3$, ppm): 1.37(3H, t, J=7 Hz), 2.85(6H, s), 3.97(2H, s), 4.82(2H, q, J=7 Hz), 6.20–6.40(2H, m), 6.50(1H, s), 7.27(1H, d, J=10 Hz), 7.78(1H, dd, J=2, 10 Hz), 8.10–8.30(2H, m), 12.30(1H, br.s).

(20) 6,7-Dimethyl-2-[(4-dimethylamino-2-pyridyl)methylthio]indole
m.p. 134°–137° C.
IR (KBr, cm$^{-1}$): 2880, 1600, 1440, 1385, 1005, 805.
NMR (CDCl$_3$, ppm): 2.34(3H, s), 2.41(3H, s), 2.33(6H, s), 3.94(2H, s), 6.20–6.50(3H, m), 6.78(1H, d, J=8 Hz), 7.18(1H, d, J=8 Hz), 8.18–8.30(1H, m), 11.90(1H, br.s).

(21) 2-[(5-Methyl-4-piperidino-2-pyridyl)methylthio]-5-methoxy indole
m.p. 100°–101° C.
IR (KBr, cm$^{-1}$): 2930, 1600, 1260, 1235, 1170.
NMR (CDCl$_3$, ppm): 1.40–1.90(6H, m), 2.20(3H, s), 2.60–3.10(4H, m), 3.80(3H, s), 4.03(2H, s), 6.45(1H, m), 6.54(1H, s), 6.79(1H, dd, J=2, 9 Hz), 6.97(1H, d, J=2 Hz), 7.23(1H, d, J=9 Hz), 8.28(1H, s).

(22) 2-[(4-Piperidino-2-pyridyl)methylthio]indole
m.p. 130°–131° C.
IR (KBr, cm$^{-1}$): 2930, 1600, 1535, 1500, 1275, 990.
NMR (CDCl$_3$, ppm): 1.30–1.80(6H, m), 3.00–3.50(4H, m), 3.99(2H, s), 6.30–6.60(3H, m), 6.80–7.60(4H, m).

(23) 2-{[4-(4-Methylpiperazino-2-pyridyl]methylthio}indole
m.p. 163°–164° C.
IR (KBr, cm$^{-1}$): 2820, 1615, 1275, 1160, 1010.
NMR (CDCl$_3$, ppm): 2.26(3H, s), 2.20–2.70(4H, m), 3.00–3.50(4H, m), 4.00(2H, s), 6.20–6.70(3H, m), 6.90–7.60(4H, m), 8.28(1H, d, J=6 Hz).

(24) 5-Fluoro-2-[(3,5-dimethyl-4-methoxy-2-pyridyl)methylthio]indole
m.p. 109°–111° C.
IR (KBr, cm$^{-1}$): 1560, 1410, 1260, 1210, 1140, 1070, 1000, 950, 850, 790, 770.
NMR (DMSO-d$_6$, ppm): 2.19(3H, s), 2.21(3H, s), 3.71(3H, s), 4.33(2H, s), 6.46(1H, br.s), 6.92(1H, ddd, J=9, 9 Hz), 7.20(1H, dd, J=9, 3 Hz), 7.32(1H, dd, J=9, 6 Hz), 8.15(1H, s), 11.70(1H, s).

(25) 2-(2-Pyridylmethylthio-5-methoxyindole
m.p. 101°–102° C.
IR (KBr. cm$^{-1}$): 1580, 1420, 1330, 1290, 1215, 1190, 1150, 1020.
NMR (DMSO-d$_6$, ppm): 3.73(3H, s), 4.30(2H, s), 6.33(1H, br.s), 6.74(1H, dd, J=8, 2 Hz), 6.93(1H, d, J=2 Hz), 7.24(3H, m), 7.7(1H, dd, J=8, 8 Hz), 8.48(1H, d, J=4 Hz), 11.45(1H, br.s).

(26) 2-(3-Pyridylmethylthio)-5-methoxyindole
m.p. 106°–108° C.
IR (Kbr, cm$^{-1}$): 1565, 1480, 1410, 1320, 1280, 1210, 1180, 1150, 1020, 820, 800, 770.
NMR (DMSO-d$_6$, ppm): 3.76(3H, s), 4.19(2H, s), 6.33(1H, s), 6.76(1H, dd, J=9, 2 Hz), 6.94(1H, d, J=2 Hz), 7.23(1H, d, J=9 Hz), 7.26(1H, dd, J=7, 4 Hz), 7.51(1H, d, J=7 Hz), 7.38(1H, s), 7.40(1H, d, J=4 Hz), 11.44(1H, s).

(27) 2-(4-Pyridylmethylthio)-5-methoxyindole
m.p. 129°–131° C.
IR (KBr, cm$^{-1}$): 1590, 1420, 1400, 1340, 1220, 1150, 1020, 820, 800, 780.
NMR (DMSO-d$_6$, ppm): 3.74(3H, s), 4.17(2H, s), 6.34(1H, br.s), 6.73(1H, dd, J=8, 2 Hz), 6.93(1H, d, J=2 Hz), 7.20(1H, d, J=8 Hz), 7.22(2H, d, J=5 Hz), 8.45(2H, d, J=5 Hz), 11.3(1H, br.s).

(28) 2-[(3,5-Dimethyl-4-methoxy-2-pyridyl)methylthio]indole
m.p. 125°–127° C.
IR (KBr, cm$^{-1}$): 1565, 1470, 1440, 1410, 1340, 1260, 1120, 1060, 1000, 750, 730.
NMR (DMSO-d$_6$, ppm): 2.16(3H, s), 2.18(3H, s), 3.70(3H, s), 4.30(2H, s), 6.45(1H, br.s), 6.95(1H, dd, J=6, 6 Hz), 7.09(1H, dd, J=6, 6 Hz), 7.33(1H, d, J=6 Hz), 7.43(1H, d, J=6 Hz), 8.13(1H, s), 11.35(1H, s).

(29) 3-Methyl-2-[(3,5-dimethyl-4-methoxy-2-pyridyl)methylthio]indole
m.p. 150°–151° C.
IR (KBr, cm$^{-1}$): 1470, 1440, 1345, 1330, 1260, 1110, 1060, 1000, 740.
NMR (DMSO-d$_6$, ppm): 2.00(3H, s), 2.02(3H, s), 2.18(3H, s), 3.63(3H, s), 4.13(2H, s), 6.95(1H, dd, J=6, 6 Hz), 7.12(1H, dd, J=6, 6 Hz), 7.30(1H, d, J=6 Hz), 7.40(1H, d, J=6 Hz), 8.09(1H, s), 11.30(1H, s).

(30) 5-Methyl-2-[(3,5-dimethyl-4-methoxy-2-pyridyl)methylthio]indole
m.p. 110°–112° C.
IR (KBr, cm$^{-1}$): 1555, 1460, 1425, 1390, 1320, 1260, 1215, 1070, 990, 860, 790.

NMR (CDCl₃, ppm): 2.20(3H, s), 2.26(3H, s), 2.31(3H, s), 3.72(3H, s), 4.20(2H, s), 6.44(1H, s), 6.96(1H, d, J=9 Hz), 7.22(1H, d, J=9 Hz), 7.30(1H, s) 8.28(1H, s), 10.25(1H, s).

(31) 5-Trifluoromethyl-2-[(3,5-dimethyl-4-methoxy-2-pyridyl)methylthio]indole
m.p. 131°–132° C.
IR (KBr, cm⁻¹): 1320, 1260, 1140, 1070, 1040, 800.
NMR (DMSO-d₆, ppm): 2.20(6H, s), 3.70(3H, s), 4.36(2H, s), 6.64(1H, s), 7.35(1H, d, J=9 Hz), 7.42(1H, d, J=9 Hz), 7.83(1H, s), 8.14(1H, s), 12.03(1H, s).

(32) 2-[(3,5-Dimethyl-4-methoxy-2-pyridyl)methylthio]-5-methoxyindole
m.p. 130°–131° C.
IR (KBr, cm⁻¹): 1430, 1340, 1265, 1220, 1190, 1155, 1080, 1020, 850, 790.
NMR (DMSO-d₆, ppm): 2.13(3H, s), 2.19(3H, s), 3.69(3H, s), 3.73(3H, s), 4.27(2H, s), 6.37(1H, br.s), 6.74(1H, dd, J=9, 2 Hz), 6.93(1H, d, J=2 Hz), 7.22(1H, d, J=9 Hz), 8.15(1H, s), 11.40(1H, s).

(33) 2-[(3,5-Dimethyl-4-methoxy-2-pyridyl)methylthio]-5-methoxycarbonylindole
m.p. 172°–173° C.
IR (KBr, cm⁻¹): 1680, 1430, 1310, 1260, 1190, 1120, 1080, 770.
NMR (DMSO-d₆, ppm): 2.19(6H, s), 3.68(3H, s), 3.83(3H, s), 4.33(2H, s), 6.60(1H, s), 7.36(1H, d, J=8 Hz), 7.72(1H, d, J=8 Hz), 8.11(1H, s), 8.12(1H, s), 11.95(1H, s).

(34) 5-Acetyl-2-[(3,5-dimethyl-4-methoxy-2-pyridyl)methylthio]indole
m.p. 149°–151° C.
IR (KBr, cm⁻¹): 1640, 1350, 1340, 1290, 1240, 1070, 800.
NMR (DMSO-d₆, ppm): 2.20(6H, s), 2.60(3H, s), 3.70(3H, s), 4.35(2H, s), 6.65(1H, br.s), 7.38(1H, d, J=9 Hz), 7.75(1H, d, J=9 Hz), 8.14(1H,s), 8.18(1H, s), 12.0(1H, br.s).

(35) 3-Methylthio-2-[(3,5-dimethyl-4-methoxy-2-pyridyl)methylthio]indole
m.p. 167°–168° C.
IR (KBr, cm⁻¹): 1460, 1420, 1330, 1250, 1110, 1050, 980, 735.
NMR (DMSO-d₆, ppm): 2.15(3H, s), 2.19(3H, s), 2.22(3H, s), 3.70(3H, s), 4.37(2H, s), 7.0–7.6(4H, m), 8.10(1H, s), 11.95(1H, br.s).

(36) 7-Trifluoromethyl-2-[(3,5-dimethyl-4-methoxy-2-pyridyl)methylthio]indole
m.p. 74° C.
IR (KBr, cm⁻¹): 1430, 1320, 1300, 1180, 1140, 1105, 1080, 800, 730.
NMR (DMSO-d₆, ppm): 2.20(6H, s), 3.70(3H, s), 4.38(2H, s), 6.63(1H, br.s), 7.13(1H, dd, J=8, 8 Hz), 7.41(1H, d, J=8 Hz), 7.73(1H, d, J=8 Hz), 8.18(1H, s), 12.2(1H, br.s).

EXAMPLES 37–47

The following compounds of Examples Nos. (37) to (47) were prepared in the same manner as described in Example 2.

(37) 3-[(4-Chloro-2-pyridyl)methylthio]indole
m.p. 126°–128° C.
IR (KBr, cm⁻¹): 3160, 2900, 1580, 1495, 1425, 1390, 1340, 1240, 1100.
NMR (DMSO-d₆, ppm): 3.90(2H, s), 6.90–7.50(7H, m), 8.28(1H, d, J=5 Hz), 11.25(1H, br.s).

(38) 3-[(4-Ethoxycarbonyl-2-pyridyl)methylthio]indole
It was in the form of an oil.
IR (CHCl₃ solution, cm⁻¹): 2950, 1780, 1600, 1200, 1020, 900.
NMR (CDCl₃, ppm): 1.40(3H, t, J=7 Hz), 3.85(2H, s), 4.45(2H, q, J=7 Hz), 6.90–8.00(7H, m), 8.48(1H, d, J=7 Hz), 9.15(1H, br.s).

(39) 3-[(4-Hydroxy-2-pyridyl)methylthio]indole
m.p. 191°–192° C.
IR (KBr, cm⁻¹): 3200, 2900, 1620, 1515, 1490, 1420, 1245, 1160, 865.
NMR (DMSO-d₆, ppm): 3.70(2H, s), 4.75(2H, br.s), 5.95(1H, s), 6.20(1H, d, J=7 Hz), 6.90–7.90(5H, m).

(40) 3-[(5-Methyl-4-piperidino-2-pyridyl)methylthio]indole
m.p. 170°–171° C.
IR (KBr, cm⁻¹): 1605, 1460, 1410, 1235, 1055, 1010, 990.
NMR (DMSO-d₆, ppm): 1.30–1.70(6H, m), 2.08(3H, s), 2.40–2.80(4H, m), 3.83(2H, s), 6.29(1H, s), 6.90–7.60(5H, m).

(41) 3-[(4-Piperidino-2-pyridyl)methylthio]indole
m.p. 145°–147° C.
IR (KBr, cm⁻¹): 2930, 1605, 1510, 990, 750.
NMR (DMSO-d₆, ppm): 1.1–1.8(6H, m), 2.7–3.4(4H, m), 3.88(2H, s), 6.25(1H, d, J=2 Hz), 6.43(1H, dd, J=2, 6 Hz), 6.8–7.7(5H, m), 8.08(1H, d, J=6 Hz), 10.3(1H, br.s).

(42) 3-[(2-Pyridyl)methylthio]indole
m.p. 124°–125° C.
IR (KBr, cm⁻¹): 3150, 3120, 3080, 2900, 1600, 1445, 1005, 790, 740.
NMR (CDCl₃, ppm): 3.94(2H, s), 6.8–7.2(6H, m), 7.2–7.6(2H, m), 8.2–8.4(1H, m), 9.6(1H, br.s).

(43) 5-Fluoro-3-[(3,5-dimethyl-4-methoxy-2-pyridyl)methylthio]indole
m.p. 178° C.
IR (KBr, cm⁻¹): 1550, 1450, 1260, 1210, 1140, 1060, 990, 920, 845, 785.
NMR (DHSO-d₆, ppm): 2.02(3H, s), 2.16(3H, s), 3.50(3H, s), 3.96(2H, s), 6.75–7.05(2H, m), 7.30–7.50(2H, m), 8.04(1H, s), 11.50(1H, s).

(44) 3-[(3,5-Dimethyl-4-methoxy-2-pyridyl)methylthio]indole
m.p. 121°–122° C.
IR (KBr, cm⁻¹): 1565, 1480, 1450, 1440, 1265, 1230, 1080, 1010, 745.
NMR (DMSO-d₆, ppm): 2.06(3H, s), 2.18(3H, s), 3.62(3H, s), 4.00(2H, s), 7.10(2H, m), 7.40(3H, m), 8.07(1H, s), 11.50(1H, s).

(45) 2-Methyl-3-[(3,5-dimethyl-4-methoxy-2-pyridyl)methylthio]indole
m.p. 185°–187° C.
IR (KBr, cm⁻¹): 1260, 1225, 1080, 1000, 730.
NMR (DMSO-d₆, ppm): 1.97(3H, s), 2.13(3H, s), 2.16(3H, s), 3.57(3H, s), 3.86(2H, s), 7.00(2H, m), 7.30(2H, m), 8.03(1H, s), 11.40(1H, s).

(46) 3-[(3,5-Dimethyl-4-methoxy-2-pyridyl)methylthio]-5-methoxyindole
m.p. 170°–172° C.
IR (KBr, cm⁻¹): 1450, 1260, 1190, 1160, 1060, 1020, 980, 900, 830, 790.
NMR (DMSO-d₆, ppm): 1.95(3H, s), 2.15(3H, s), 3.52(3H, s), 3.70(3H, s), 3.94(2H, s), 6.65(1H, s), 6.70(1H, d, J=9 Hz), 7.27(1H, d, J=9 Hz), 7.30(1H, s), 8.06(1H, s), 11.35(1H, s).

(47) 3-[(3,5-Dimethyl-4-methoxy-2-pyridyl)methylthio]-5-methoxycarbonylindole
m.p. 194°–197° C.

IR (KBr, cm$^{-1}$): 1700, 1440, 1290, 1260, 1230, 1220, 1200, 1070, 1000, 810, 770.

NMR (DMSO-d$_6$, ppm): 1.94(3H, s), 2.13(3H, s), 3.50(3H, s), 3.90(3H, s), 4.00(2H, s), 7.46(1H, d, J=9 Hz), 7.56(1H, br.s), 7.74(1H, d, J=9 Hz), 7.80(1H, s), 8.05(1H, s), 11.90(1H, br.s).

EXAMPLES 48–63

The following compound of Examples Nos (48) to (63) were prepared in the same manner as described in Example 3.

(48) 1-Methyl-2-[(5-methyl-4-piperidino-2-pyridyl)methylsulfinyl]indole

It was in the form of an oil.

IR (CHCl$_3$ solution, cm$^{-1}$): 2900, 1600, 1260, 1245, 1235, 1070, 1050, 760.

NMR (CDCl$_3$, ppm): 1.20–1.70(6H, m), 2.13(3H, s), 2.30–2.80(4H, m), 3.72(3H, s), 4.35(1H, d, J=12Hz), 4.69(1H, d, J=12Hz), 6.26(1H, s), 6.86(1H, s), 6.90–8.00(4H, m), 8.12(1H, s).

(49) 5-Fluoro-2-[(3,5-dimethyl-4-methoxy-2-pyridyl)methylsulfinyl]indole m.p. 192°–195° C. (with decomposition).

IR (KBr, cm$^{-1}$): 1560, 1460, 1435, 1150, 1070, 1000, 800.

NMR (DMSO-d$_6$, ppm): 2.11(3H, s), 2.19(3H, s), 3.65(3H, s), 4.63(2H, ABq, J=13 Hz), 6.80(1H, br.s), 7.10(1H, ddd, J=9,9, 3 Hz), 7.35(1H, dd, J=9, 3 Hz), 7.51(1H, dd, J=9, 6 Hz), 8.20(1H, s), 12.40(1H, s).

(50) 2-(2-Pyridylmethylsulfinyl)-5-methoxyindole m.p. 168°–169° C.

IR (KBr, cm$^{-1}$): 1500, 1430, 1190, 1155, 1005.

NMR (DMSO-d$_6$, ppm): 3.77(3H, s), 4.64(2H, ABq, J=13 Hz), 6.75(1H, br.s), 6.89(1H, dd, J=9, 2 Hz), 7.08(1H, d, J=2 Hz), 7.33(3H, m), 7.72(1H, dd, J=7, 7 Hz), 8.53(1H, d, J=5 Hz), 12.2(1H, br.s).

(51) 2-(3-Pyridylmethylsulfinyl)-5-methoxyindole m.p. 178°–180° C.

IR (KBr, cm$^{-1}$): 1490, 1440, 1420, 1410, 1280, 1210, 1150, 1010, 1000, 835, 790.

NMR (DMSO-d$_6$, ppm): 3.76(3H, s), 4.52(2H, s), 6.70(1H, s), 6.91(1H, dd, J=9, 2 Hz), 7.07(1H, d, J=2 Hz), 7.28(1H, dd, J=8, 5 Hz), 7.40(1H, d, J=9 Hz), 7.55(1H, d, J=8 Hz), 8.28(1H, s), 8.45(1H, d, J=5 Hz), 11.86(1H, s).

(52) 2-(4-Pyridylmethylsulfinyl)-5-methoxyindole m.p. 188°–190° C. (with decomposition).

IR (KBr, cm$^{-1}$): 1590, 1500, 1440, 1405, 1220, 1190, 1160, 1040, 840, 810.

NMR (DMSO-d$_6$, ppm): 3.78(3H, s), 4.53(2H, s), 6.73(1H, br.s), 6.92(1H, dd, J=9, 2 Hz), 7.06(1H, d, J=2 Hz), 7.17(2H, d, J=5 Hz), 7.40(1H, d, J=9 Hz), 8.47(2H, d, J=5 Hz), 12.1(1H, br.s).

(53) 2-[(3,5-Dimethyl-4-methoxy-2-pyridyl)methylsulfinyl]indole m.p. 200°–203° C. (with decomposition).

IR (KBr, cm$^{-1}$): 1560, 1460, 1420, 1340, 1285, 1260, 1090, 1070, 1005, 800, 750, 730.

NMR (DMSO-d$_6$, ppm): 2.12(3H, s), 2.18(3H, s), 3.63(3H, s), 4.63(2H, ABq, J=13 Hz), 6.80(1H, br.s), 7.06(1H, dd, J=6, 6 Hz), 7.25(1H, dd, J=6, 6 Hz), 7.51(1H, d, J=6 Hz), 7.59(1H, d, J=6 Hz), 8.20(1H, s), 12.32(1H, s).

(54) 3-Methyl-2-[(3,5-dimethyl-4-methoxy-2-pyridyl)methylsulfinyl]indole m.p. 158°–159° C.

IR (KBr, cm$^{-1}$): 1460, 1440, 1200, 1065, 1000, 740.

NMR (DMSO-d$_6$, ppm): 1.96(3H, s), 2.02(3H, s), 2.17(3H, s), 3.56(3H, s), 4.62(2H, ABq, J=13 Hz), 7.05(1H, dd, J=6, 6 Hz), 7.47(1H, d, J=6 Hz), 7.51(1H, d, J=6 Hz), 8.18(1H, s), 12.03(1H, s).

(55) 5-Methyl-2-[(3,5-dimethyl-4-methoxy-2-pyridyl)methylsulfinyl]indole m.p. 189°–191° C. (with decomposition).

IR (KBr, cm$^{-1}$): 1560, 1460, 1440, 1300, 1085, 1070, 1010, 810.

NMR (DMSO-d$_6$, ppm): 2.13(3H, s), 2.20(3H, s), 2.38(3H, s), 3.66(3H, s), 4.64(2H, ABq, J=13 Hz), 6.70(1H, br.s), 7.08(1H, d, J=8 Hz), 7.37(1H, s), 7.40(1H, d, J=8 Hz), 8.20(1H, s), 12.2(1H, br.s).

(56) 5-Trifluoromethyl-2-[(3,5-dimethyl-4-methoxy-2-pyridyl)methylsulfinyl]indole m.p. 218° C. (with decomposition).

IR (KBr, cm$^{-1}$): 1340, 1320, 1270, 1150, 1100, 1070, 1045, 1000, 800.

NMR (DMSO-d$_6$, ppm): 2.14(3H, s), 2.20(3H, s), 3.67(3H, s), 4.67(2H, ABq, J=13 Hz), 6.98(1H, s), 7.52(1H, d, J=9 Hz), 7.71(1H, d, J=9 Hz), 8.03(1H, s), 8.20(1H, s), 12.75(1H, s).

(57) 2-[(3,5-Dimethyl-4-methoxy-2-pyridyl)methylsulfinyl]-5-methoxyindole m.p. 170°–171° C.

IR (KBr, cm$^{-1}$): 1460, 1200, 1160, 1070, 1000, 855, 800.

NMR (DMSO-d$_6$, ppm): 2.10(3H, s), 2.18 (3H, s), 3.63(3H, s), 3.75(3H, s), 4.60(2H, ABq, J=13 Hz), 6.70(1H, br.s), 6.90(1H, dd, J=9, 2 Hz), 7.05(1H, d, J=2 Hz), 7.38(1H, d, J=9 Hz), 8.20(1H, s), 12.13(1H, s).

(58) 2-[(3,5-Dimethyl-4-methoxy-2-pyridyl)methylsulfinyl]-5-methoxycarbonylindole m.p. 205°–208° C.

IR (KBr, cm$^{-1}$): 1700, 1430, 1300, 1250, 1200, 1120, 1100, 1070, 1010, 770.

NMR (DMSO-d$_6$, ppm): 2.12(3H, s), 2.18(3H, s), 3.65(3H, s), 3.87(3H, s), 4.64(2H, ABq, J=13 Hz), 6.96(1H, s), 7.55(1H, d, J=9 Hz), 7.85(1H, d, J=9 Hz), 8.18(1H, s), 8.30(1H, s), 12.66(1H, s).

(59) 5-Acetyl-2-[(3,5-dimethyl-4-methoxy-2-pyridyl)methylsulfinyl]indole m.p. 205° C.

IR (KBr, cm$^{-1}$): 1660, 1300, 1250, 1070, 1000, 820

NMR (DMSO-d$_6$, ppm): 2.13(3H, s), 2.20(3H, s), 2.62(3H, s), 3.67(3H, s), 4.68(2H, ABq, J=13 Hz), 7.00(1H, s), 7.56(1H, d, J=9 Hz), 7.88(1H, d, J=9 Hz), 8.20(1H, s), 8.35(1H, s), 12.7(1H, br.s).

(60) 7-Trifluoromethyl-2-[(3,5-dimethyl-4-methoxy-2-pyridyl)methylsulfinyl]indole m.p. 153°–156° C.

IR (KBr, cm$^{-1}$): 1320, 1300, 1190, 1150, 1100, 1010.

NMR (DMSO-d$_6$, ppm): 2.20(6H, s), 3.67(3H, s), 4.78(2H, s), 7.12(1H, s), 7.27(1H, dd, J=8, 8 Hz), 7.63(1H, d, J=8 Hz), 7.96(1H, d, J=8 Hz), 8.22(1H, s), 12.6(1H, br.s).

(61) 3-[(3,5-Dimethyl-4-methoxy-2-pyridyl)methylsulfinyl]indole m.p. 176°–177° C.

IR (KBr, cm$^{-1}$): 1560, 1470, 1460, 1430, 1280, 1245, 1075, 1005, 750.

NMR (DMSO-d$_6$, ppm): 2.10(3H, s), 2.20(3H, s), 3.65(3H, s), 4.43(2H, ABq, J=12 Hz), 7.22(2H, m), 7.55(1H, d, J=9 Hz), 7.82(2H, m), 8.20(1H, s), 11.97(1H, s).

(62) 2-Methyl-3-[(3,5-dimethyl-4-methoxy-2-pyridyl)methylsulfinyl]indole m.p. 107°–109° C.

IR (KBr, cm$^{-1}$): 1290, 1080, 1070, 1005, 990, 755.

NMR (DMSO-d$_6$, ppm): 1.95(3H, s), 2.20(6H, s), 3.60(3H, s), 4.50(2H, ABq, J=13 Hz), 7.12(2H, m), 7.39(1H, dd, J=5, 5 Hz), 7.88(1H, d, J=5 Hz), 8.16(1H, s), 11.71(1H, s).

(63) 5-Methoxycarbonyl-3-[(3,5-dimethyl-4-methoxy-2-pyridyl)methylsulfinyl]indole m.p. 152°–154° C.

IR (KBr, cm$^{-1}$): 1720, 1470, 1430, 1310, 1250, 1220, 1090, 1080, 995.

NMR (DMSO-d$_6$, ppm): 1.96(3H, s), 2.15(3H, s), 3.52(3H, s), 3.90(3H, s), 4.60(2H, ABq, J=13 Hz), 7.58(1H, d, J=9 Hz), 7.84(1H, d, J=9 Hz), 7.92(1H, br.s), 8.16(1H, s), 8.20(1H, s), 12.3(1H, br.s).

What is claimed is:

1. A compound of the formula (I)

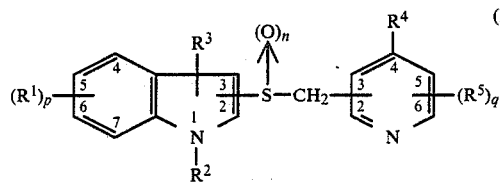

wherein $R^1$ is a hydrogen atom, a halogen atom, a lower alkyl group, a trifluoromethyl group, a lower alkoxy group, a lower alkanoyl group or a lower alkoxycarbonyl group; $R^2$ is a hydrogen atom or a lower alkyl group; $R^3$ is a hydrogen atom, a lower alkyl group, a lower alkoxy group or a lower alkylthio group; $R^4$ is a hydrogen atom, a lower alkyl group, a lower alkoxy group, a halogen atom, a hydroxy group, a lower alkoxycarbonyl group, a phenyl-(C$_1$-C$_4$)alkyloxy group, or a group of the formula —NR$^a$R$^b$ where R$^a$ and R$^b$ are the same or different and each are a hydrogen atom or a lower alkyl group, or R$^a$ and R$^b$ taken together with the adjacent nitrogen atom form a heterocyclic group selected from the group consisting of a pyrrolidino group, a piperdino group, a morpholino group, a thiomorpholino group or a piperazino group of which the heterocyclic group is unsubstituted or substituted with a lower alkyl group; $R^5$ is a hydrogen atom, a lower alkyl group, a lower alkoxy group, a phenyl-(C$_1$-C$_4$)alkyl group or a naphthyl(C$_1$-C$_4$)alkyl group or a phenyl-(C$_1$-C$_4$)alkyloxy group; and n is an integer of zero or 1, p is an integer of 1, 2, 3 or 4; and q is an integer of 1, 2 or 3, or pharmaceutically acceptable salt of said compound.

2. A compound as claimed in claim 1, which is of the formula (I')

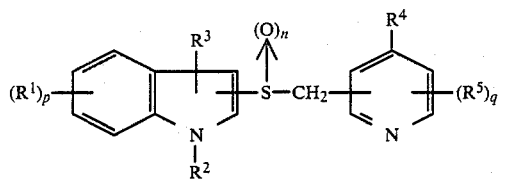

wherein $R^1$ is a hydrogen atom, a halogen atom, a lower alkyl group, a trifluoromethyl group, a lower alkoxy group, a lower alkanoyl group or a lower alkoxycarbonyl group; $R^2$ is a hydrogen atom or a lower alkyl group; $R^3$ is a hydrogen atom, a lower alkyl group or a lower alkylthio group; $R^4$ is a hydrogen atom, a lower alkyl group, a lower alkoxy group, a halogen atom, a hydroxy group, a lower alkoxycarbonyl group, an amino group, a mono-lower-alkyl-amino group, a dilower-alkylamino group, or $R^4$ is a pyrrolidino group, a piperidino group, a morpholino group, a thiomorpholino group or a piperazino group of which the heterocyclic group is unsubstituted or substituted by a lower alkyl group; $R^5$ is a hydrogen atom, a lower alkyl group or a lower alkoxy group; and n is zero or 1; p is 1, 2, 3 or 4; and q is 1, 2 or 3, or a pharmaceutically acceptable salt of said compound.

3. A compound as claimed in claim 1 which is of the formula (I-1)

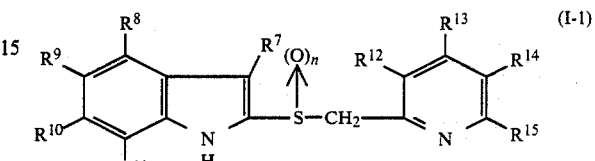

wherein $R^7$ is a hydrogen atom, an alkyl group of 1–6 carbon atoms or an alkylthio group of 1–6 carbon atoms; $R^8$, $R^9$, $R^{10}$ and $R^{11}$ are the same or different and each are a hydrogen atom, a halogen atom, an alkyl group of 1–6 carbon atoms, a trifluoromethyl group, an alkoxy group of 1–6 carbon atoms, an alkanoyl group of 2–6 carbon atoms or an alkoxycarbonyl group of 2–6 carbon atoms; $R^{12}$, $R^{13}$, $R^{14}$ and $R^{15}$ are the same or different and each are a hydrogen atom, an alkyl group of 1–6 carbon atoms or an alkoxy group of 1–6 carbon atoms; and n is zero or 1, or a pharmaceutically acceptable salt of said compound.

4. A compound as claimed in claim 3, in which $R^7$ is a hydrogen atom, a methyl group or a methylthio group; $R^8$ and $R^{10}$ each are a hydrogen atom; $R^9$ is a hydrogen atom, a halogen atom, an alkyl group of 1–6 carbon atoms, a trifluoromethyl group, an alkoxy group of 1–6 carbon atoms, an alkanoyl group of 2–6 carbon atoms or an alkoxycarbonyl group of 2–6 carbon atoms; $R^{11}$ is a hydrogen atom or a trifluoromethyl group; $R^{12}$ and $R^{14}$ each are a hydrogen atom or an alkyl group of 1–6 carbon atoms; and $R^{13}$ is an alkoxy group of 1–6 carbon atoms; $R^{15}$ is a hydrogen atom; and n is zero or 1.

5. A compound as claimed in claim 1, which is of the formula (I-2)

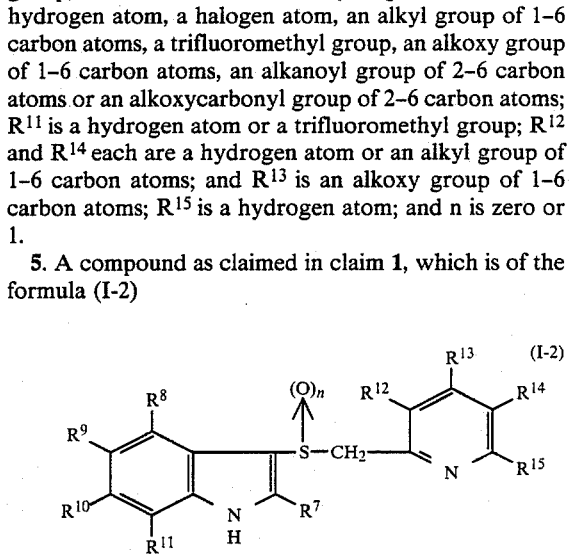

wherein $R^7$ is a hydrogen atom or an alkyl group of 1–6 carbon atoms; $R^8$, $R^9$, $R^{10}$ and $R^{11}$ are the same or different and each are a hydrogen atom, a halogen atom, an alkyl group of 1–6 carbon atoms, a trifluoromethyl group, an alkoxy group of 1–6 carbon atoms, an alkanoyl group of 2–6 carbon atoms or an alkoxycarbonyl group of 2–6 carbon atoms; $R^{12}$, $R^{13}$, $R^{14}$ and $R^{15}$ are the same or different and each are a hydrogen atom, an alkyl group of 1–6 carbon atoms or an alkoxy group of 1-6 carbon atoms; n is zero or 1, or a pharmaceutically acceptable salt of said compound.

6. A compound as claimed in claim 5, in which $R^7$ is a hydrogen atom or a methyl group; $R^8$ and $R^{10}$ are each a hydrogen atom; $R^9$ is a hydrogen atom, a halogen atom, an alkyl group of 1-6 carbon atoms, a trifluoromethyl group, an alkoxy group of 1-6 carbon atoms, an alkanoyl group of 2-6 carbon atoms, or an alkoxycarbonyl group of 2-6 carbon atoms; $R^{11}$ is a hydrogen atom or a trifluoromethyl group; $R^{12}$ and $R^{14}$ are each a hydrogen atom or an alkyl group of 1-6 carbon atoms; and $R^{13}$ is an alkoxy group of 1-6 carbon atoms; $R^{15}$ is a hydrogen atom; and n is zero or 1.

7. A compound as claimed in claim 1 which is of the formula (I-3)

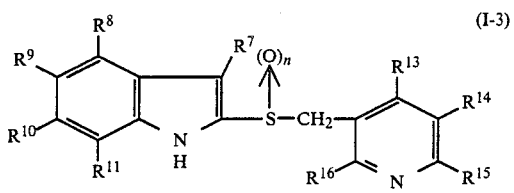

wherein $R^7$ is a hydrogen atom, an alkyl group of 1-6 carbon atoms or an alkylthio group of 1-6 carbon atoms; $R^8$, $R^9$, $R^{10}$ and $R^{11}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{13}$, $R^{14}$, $R^{15}$ and $R^{16}$ are the same or different and each are a hydrogen atom, an alkyl group of 1-6 carbon atoms or an alkoxy group of 1-6 carbon atoms; and n is zero or 1, or a pharmaceutically acceptable salt of said compound.

8. A compound as claimed in claim 7, in which $R^7$ is a hydrogen atom, a methyl group or a methylthio group; $R^8$, $R^{10}$ and $R^{11}$ are each a hydrogen atoms; $R^9$ is a hydrogen atom, an alkyl group of 1-6 carbon atoms, a trifluoromethyl group, an alkoxy group of 1-6 carbon atoms, an alkanoyl group of 2-6 carbon atoms, or an alkoxycarbonyl group of 2-6 carbon atoms; $R^{13}$ is a hydrogen atom, an alkyl group of 1-6 carbon atoms or an alkoxy group of 1-6 carbon atoms; and $R^{14}$, $R^{15}$ and $R^{16}$ each are a hydrogen atom; and n is zero or 1.

9. A compound as claimed in claim 1, which is of the formula (I-4)

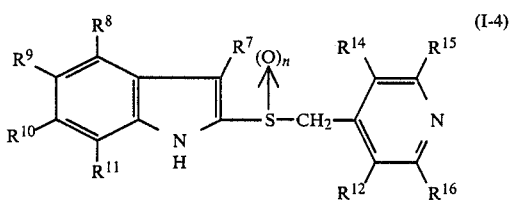

wherein $R^7$ is a hydrogen atom, a methyl group or a methylthio group; $R^8$, $R^9$, $R^{10}$ and $R^{11}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{12}$, $R^{14}$, $R^{15}$ and $R^{16}$ are the same or different and each are a hydrogen atom, an alkyl group of 1-6 carbon atoms or an alkoxy group of 1-6 carbon atoms; and n is zero or 1, or a pharmaceutically acceptable salt of said compound.

10. A compound as claimed in claim 9, in which $R^7$ is a hydrogen atom, a methyl group or a methylthio group; $R^8$, $R^{10}$ and $R^{11}$ are each a hydrogen atom; $R^9$ is a hydrogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{12}$, $R^{14}$, $R^{15}$ and $R^{16}$ are each a hydrogen atom; and n is zero or 1.

11. A compound as claimed in claim 1, which is of the formula (I-5)

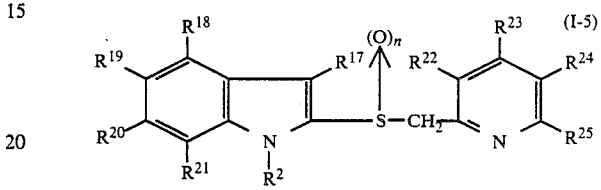

wherein $R^2$ is a hydrogen atom or an alkyl group of 1-6 carbon atoms; $R^{17}$ is a hydrogen atom or an alkyl group of 1-6 carbon atoms; $R^{18}$, $R^{19}$, $R^{20}$ and $R^{21}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{22}$, $R^{24}$ and $R^{25}$ are the same or different and each are a hydrogen atom or an alkyl group of 1-6 carbon atoms; $R^{23}$ is a group of the formula

where $R^a$ and $R^b$ are the same or different and each are a hydrogen atom or an alkyl group of 1-6 carbon atoms, or $R^a$ and $R^b$ taken together with the adjacent nitrogen atom form a heterocyclic group selected from the group consisting of pyrrolidino group, a piperidino group, a morpholino group, a thiomorpholino group or a piperazino group of which the heterocyclic group is unsubstituted or substituted with a lower alkyl group; and n is zero or 1, or a pharmaceutically acceptable salt of said compound.

12. A compound as claimed in claim 11 in which $R^2$ is a hydrogen atom or a methyl or ethyl group; $R^{17}$ is a hydrogen atom or a methyl group; $R^{18}$ is a hydrogen atom or an alkyl group of 1-6 carbon atoms; $R^{19}$ is a hydrogen atom, a halogen atom, an alkyl group of 1-6 carbon atoms, a trifluoromethyl group, an alkoxy group of 1-6 carbon atoms, an alkanoyl group of 2-6 carbon atoms, or an alkoxycarbonyl group of 2-6 carbon atoms; $R^{20}$ is a hydrogen atom, an alkyl group of 1-6 carbon atoms, an alkanoyl group of 2-6 carbon atoms or a trifluoromethyl group; $R^{21}$ is a hydrogen atom, an alkyl group of 1-6 carbon atoms or a trifluoromethyl group; $R^{22}$ and $R^{24}$ are each a hydrogen atom or an alkyl group of 1-6 carbon atoms; $R^{23}$ is an amino group or a mono- or di-$(C_1-C_6)$ alkylamino group or a 5-membered or 6-membered heterocyclic group selected from the group consisting of pyrrolidino group, a piperidino group, a morpholino group, a thiomorpholino group or a piperazino group of which the heterocyclic group is unsubstituted or substituted with a lower alkyl group; $R^{25}$ is a hydrogen atom or an alkyl group of 1-6 carbon atoms; and n is zero or 1.

13. A compound as claimed in claim 11 in which $R^{23}$ is a piperidino, pyrrolidino, morpholino, thiomorpholino or piperazino group as the heterocyclic group.

14. A compound as claimed in claim 11, in which $R^{23}$ is a group of the formula

where $R^a$ and $R^b$ are each an alkyl group of 1-6 carbon atoms.

15. A compound as claimed in claim 1, which is of the formula (I-6)

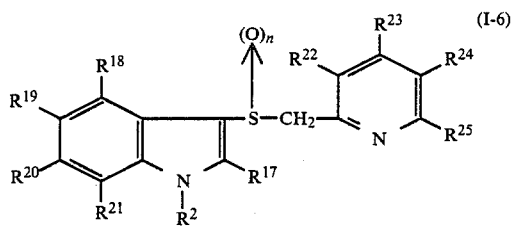

wherein $R^2$ is a hydrogen atom or an alkyl group of 1-6 carbon atoms; $R^{17}$ is a hydrogen atom or an alkyl group of 1-6 carbon atoms; $R^{18}$, $R^{19}$, $R^{20}$ and $R^{21}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{22}$, $R^{24}$ and $R^{25}$ are the same or different and each are a hydrogen atom or an alkyl group of 1-6 carbon atoms; $R^{23}$ is a group of the formula

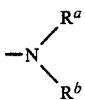

where $R^a$ and $R^b$ are each a hydrogen atom or an alkyl group of 1-6 carbon atoms, or $R^a$ and $R^b$ taken together with the adjacent nitrogen atom form a 5-membered or 6-membered heterocyclic group selected from the group consisting of pyrrolidino group, a piperidino group, a morpholino group, a thiomorpholino group or a piperazino group of which the heterocyclic group is unsubstituted or substituted with a lower alkyl group; and n is zero or 1, or a pharmaceutically acceptable salt of said compound.

16. A compound as claimed in claim 15 in which $R^2$ is a hydrogen atom or a methyl or ethyl group; $R^{17}$ is a hydrogen atom or a methyl group; $R^{18}$, $R^{20}$ and $R^{21}$ are each a hydrogen atom; $R^{19}$ is a hydrogen atom, a halogen atom, an alkyl group of 1-6 carbon atoms, a trifluoromethyl group, an alkoxy group of 1-6 carbon atoms, an alkanoyl group of 2-6 carbon atoms, or an alkoxycarbonyl group of 2-6 carbon atoms; $R^{22}$ and $R^{24}$ are each a hydrogen atom or an alkyl group of 1-6 carbon atoms; $R^{23}$ is an amino group or a mono- or di-($C_1$-$C_6$) alkylamino group or a 5-membered or 6-membered heterocyclic group selected from the group consisting of pyrrolidino group, a piperidino group, a morpholino group, a thiomorpholino group or a piperazino group of which the heterocyclic group is unsubstituted or substituted with a lower alkyl group; $R^{25}$ is a hydrogen atom; and n is zero or 1.

17. A compound as claimed in claim 15, in which $R^{23}$ is a piperidino, pyrrolidino, morpholino, thiomorpholino or piperazino group as the heterocyclic group.

18. A compound as claimed in claim 15, in which $R^{23}$ is a group of the formula

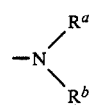

where $R^a$ and $R^b$ are each an alkyl group of 1-6 carbon atoms.

19. A compound as claimed in claim 1, which is of the formula (I-7).

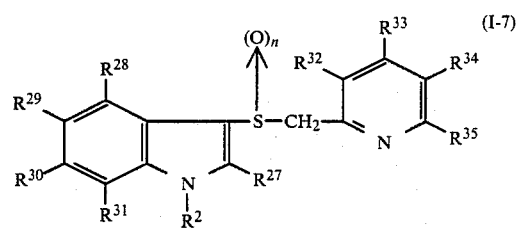

wherein $R^2$ is a hydrogen atom or an alkyl group of 1-6 carbon atoms; $R^{27}$ is a hydrogen atom or an alkyl group of 1-6 carbon atoms; $R^{28}$, $R^{29}$, $R^{30}$ and $R^{31}$ are the same or different and each are a hydrogen atom, a halogen atom, an alkyl group of 1-6 carbon atoms, a trifluoromethyl group, an alkoxy group of 1-6 carbon atoms, an alkanoyl group of 2-6 carbon atoms or an alkoxycarbonyl group of 2-6 carbon atoms; $R^{32}$, $R^{34}$ and $R^{35}$ are the same or different and each are a hydrogen atom or an alkyl group of 1-6 carbon atoms; $R^{33}$ is a halogen atom, a hydroxy group or an alkoxycarbonyl group of 2-6 carbon atoms, and n is zero or 1, or a pharmaceutically acceptable salt of said compound.

20. A compound as claimed in claim 19, in which $R^2$ is a hydrogen atom; $R^{27}$, $R^{28}$, $R^{29}$, $R^{30}$, $R^{31}$, $R^{32}$, $R^{34}$ and $R^{35}$ are each a hydrogen atom; and $R^{33}$ is a halogen atom, a hydroxy group or an alkoxycarbonyl group of 2-6 carbon atoms, and n is zero.

21. A compound as claimed in claim 1, which is selected from 5-fluoro-2-[(3,5-dimethyl-4-methoxy-2-pyridyl)methylthio]indole and 5-fluoro-3-[(3,5-dimethyl-4-methoxy-2-pyridyl)methylthio]indole.

22. A compound as claimed in claim 1, which is selected from 2-[(5-methyl-4-piperidino-2-pyridyl)methylthio]indole, 5-methyl-2-[(5-methyl-4-piperidino-2-pyridyl)methylthio]indole, 5-fluoro-2-[(5-methyl-4-piperidino-2-pyridyl)methylthio]indole, 5-acetyl-2-[(5-methyl-4-piperidino-2-pyridyl)methylthio]indole, 5-trifluoromethyl-2-[(5-methyl-4-piperidino-2-pyridyl)methylthio]indole, 5-ethoxycarbonyl-2-[(5-methyl-4-piperidino-2-pyridyl)methylthio]indole, 5-methoxy-2-[(5-methyl-4-piperidino-2-pyridyl)methylthio]indole, 3-[(4-piperidino-2-pyridyl)methylthio]indole, and 3-[(5-methyl-4-piperidino-2-pyridyl)methylthio]indole.

23. A compound as claimed in claim 1, which is selected from 2-[(4-pyrrolidino-5-methyl-2-pyridyl)methylthio]indole and 2-[(4-pyrrolidino-2-pyridyl)methylthio]indole.

24. A compound as claimed in claim 1, which is selected from 2-[(4-dimethylamino-2-pyridyl)methylthio]indole and 3-[(4-dimethylamino-2-pyridyl)methylthio]indole.

25. A pharmaceutical composion for the treatment or prevention of gastrointestinal ulcer in a mammalian animal, including man, comprising a compound of the formula (I) as defined in claim 1 or a pharmaceutically acceptable salt of said compound as the active ingredient in a therapeutically effective amount, in association with a pharmaceutically acceptable carrier for the active ingredient.

26. A method for inhibiting the gastric acid secretion and effecting the gastric cytoprotection in a mammalian animal, including human, which comprises administering to the animal suffering from the gastric acid secretion disturbances and the gastrointestinal ulcer a compound of the formula (I) as defined in claim 1 or a pharmaceutically acceptable salt of said compound in an amount effective to inhibit the gastric acid secretion and effect the gastric cytoprotection in the gastrointestines.

27. A method for the treatment or prevention of gastrointestinal ulcer in a mammalian animal, including human, suffering from or susceptible to the development of the ulcer, which comprises administering to the animal a compound of the formula (I) as defined in claim 1 or a pharmaceutically acceptable salt of said compound in an amount effective to therapeutically treat or prevent the ulcer.

28. A compound as claimed in claim 1 in which the phenyl-$(C_1-C_4)$alkoxy group for $R^4$ or $R^5$ is benzyloxy, phenethyloxy or phenylpropoxy.

29. A compound as claimed in claim 1 in which the phenyl-$(C_1-C_4)$alkyl group for $R^4$ or $R^5$ is benzyl, phenethyl or phenylpropyl, or the naphthyl-$(C_1-C_4)$-alkyl group for $R^5$ is (1-naphthyl)methyl group.

* * * * *